United States Patent [19]
Lanza et al.

[11] Patent Number: 5,958,371
[45] Date of Patent: Sep. 28, 1999

[54] SITE SPECIFIC BINDING SYSTEM, NUCLEAR IMAGING COMPOSITIONS AND METHODS

[75] Inventors: Gregory M. Lanza; Samuel A. Wickline, both of St. Louis, Mo.

[73] Assignee: Barnes-Jewish Hospital, St. Louis, Mo.

[21] Appl. No.: 08/989,979

[22] Filed: Dec. 12, 1997

Related U.S. Application Data

[63] Continuation-in-part of application No. 08/647,277, May 23, 1996, Pat. No. 5,780,010, which is a continuation-in-part of application No. 08/488,743, Jun. 8, 1995, Pat. No. 5,690,907.

[51] Int. Cl.⁶ .................................................. A61K 51/12
[52] U.S. Cl. ........................ 424/1.21; 424/1.29; 424/1.37
[58] Field of Search ................... 424/1.21, 1.17, 424/1.25, 2.29, 1.33, 1.41, 1.49, 1.53, 455; 530/367; 534/10, 14

[56] References Cited

U.S. PATENT DOCUMENTS 4,863,713   9/1989   Goodwin et al. ........................ 424/1.11
5,616,690   4/1997   Axworthy et al. ....................... 530/363

OTHER PUBLICATIONS

Urdal et al., "Tumor–associated Ganglio–N–Triosyceramide", Journal of Biological Chemistry, vol. 255, No. 21, pp. 10509–10516, 1980.

*Primary Examiner*—Jose' G. Dees
*Assistant Examiner*—Michael G. Hartley
*Attorney, Agent, or Firm*—Senniger, Powers, Leavitt & Roedel

[57] ABSTRACT

A method for ligand-based binding of lipid encapsulated particles to molecular epitopes on a surface in vivo or in vitro comprises sequentially administering (a) a site-specific ligand activated with a biotin activating agent; (b) an avidin activating agent; and (c) lipid encapsulated particles activated with a biotin activating agent, whereby the ligand is conjugated to the particles through an avidin-biotin interaction and the resulting conjugate is bound to the molecular epitopes on such surface. The conjugate is effective for imaging by x-ray, ultrasound, magnetic resonance, positron emission tomography or nuclear imaging. Compositions for use in ultrasonic imaging of natural or synthetic surfaces and for enhancing the acoustic reflectivity thereof are also disclosed.

25 Claims, 20 Drawing Sheets

FIG. 1 Aggregate Particle Size Response of Control and Biotinylated Perfluorocarbon Emulsions to Titrated Levels of Avidin FIG. 2 ULTRASONIC IMAGES OF CONTROL AND BIOTINYLATED PERFLUOROCARBON EMULSION BEFORE AND AFTER THE ADDITION OF AVIDIN GRAPHIC ILLUSTRATION OF DIALYSIS TUBING
IMAGES AND REGION OF INTEREST PLACEMENT
FOR GRAY SCALE ANALYSIS FIG. 4 Changes in Average Pixel Gray Scale Associated with the Addition of Avidin to Control or Biotinylated Perfluorocarbon Emulsion FIG. 5 The Effect of Control and Biotinylated Perfluorocarbon Emulsion on Apparent Backscatter Transfer Function and Integrated Backscatter of Avidinized Nitrocellulose Membranes FIG. 6 Apparent Backscatter Transfer Function of Biotinylated and Control Perfluorocarbon Emulsions Targeted to D-dimer Cov FIG. 7 Apparent Backscatter Transfer Function (dB) of Biotinylated and Control Perfluorocarbon Emulsions at Low Ultrasonic Fr FIG. 8  Apparent Backscatter Transfer Function of Biotinylated and Control Perfluorocarbon Large Particle Size Emulsions Targeted to Av FIG. 9
ULTRASONIC IMAGES (7.5 MHz) OF PLASMA THROMBI
PRE-TARGETED WITH ANTIFIBRIN MONOCLONAL ANTIBODY
AND EXPOSED TO CONTROL OR BIOTINYLATED PERFLUOROCARBON
EMULSION IN VITRO
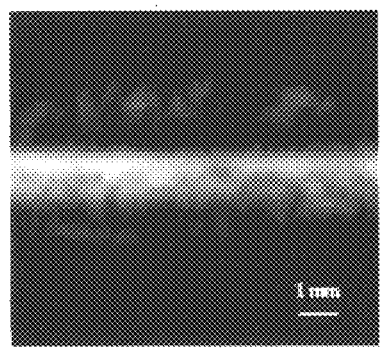
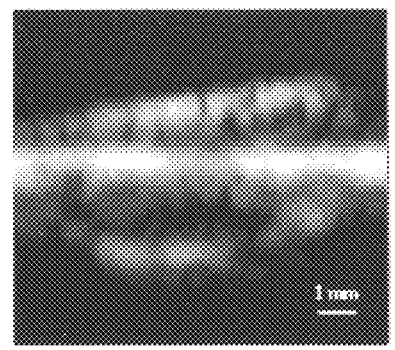
CONTROL EMULSION          BIOTINYLATED EMULSION FIG. 10  Average Pixel Grayscale of Plasma Thrombi Pre-targeted with Antifibrin Monoclonal Antibody and Exposed to Control or Biotinylated Perfluorocarbon Emulsion FIG. 11
FEMORAL ARTERY THROMBUS ACOUSTICALLY ENHANCED
WITH BIOTINYLATED PERFLUOROCARBON EMULSION IN VIVO
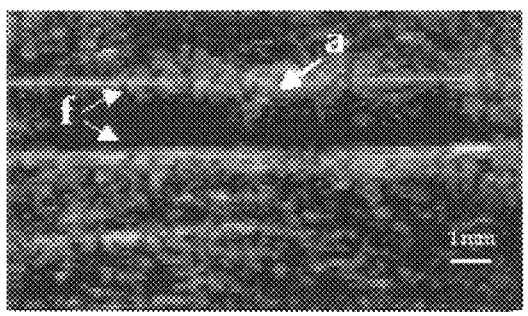 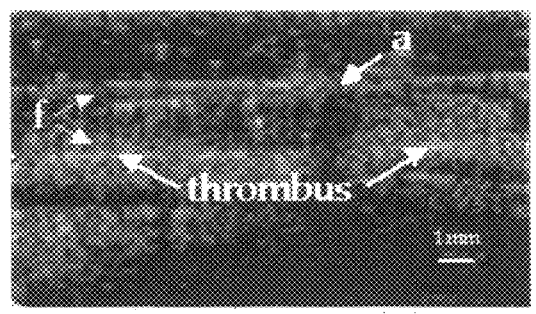
THROMBUS BEFORE TARGETED     THROMBUS AFTER TARGETED
BIOTINYLATED CONTRAST         BIOTINYLATED CONTRAST
IMAGED WITH HP SONOS 2500
7.5 MHz FOCUSED, LINEAR PHASED ARRAY TRANSDUCER
KEY: a = ELECTRICAL ANODE ; f = FEMORAL ARTERY WALLS

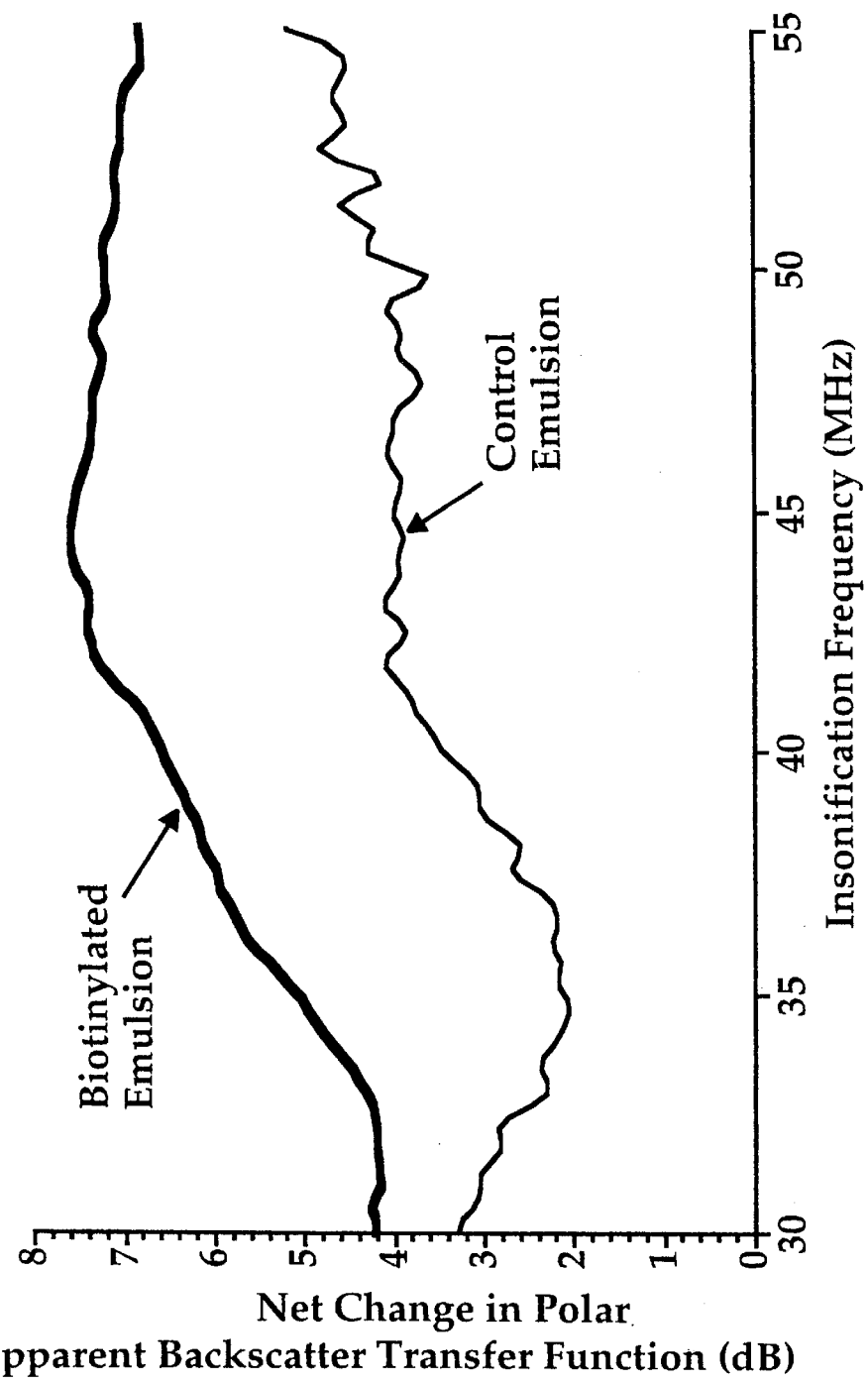
FIG. 12 Net Change in Apparent Backscatter Transfer Function of Biotinylated and Control Perfluorocarbon Emulsions Targeted to Prostate Specific Antigen in Prostatic Carcinoma Relative to Normal Regions

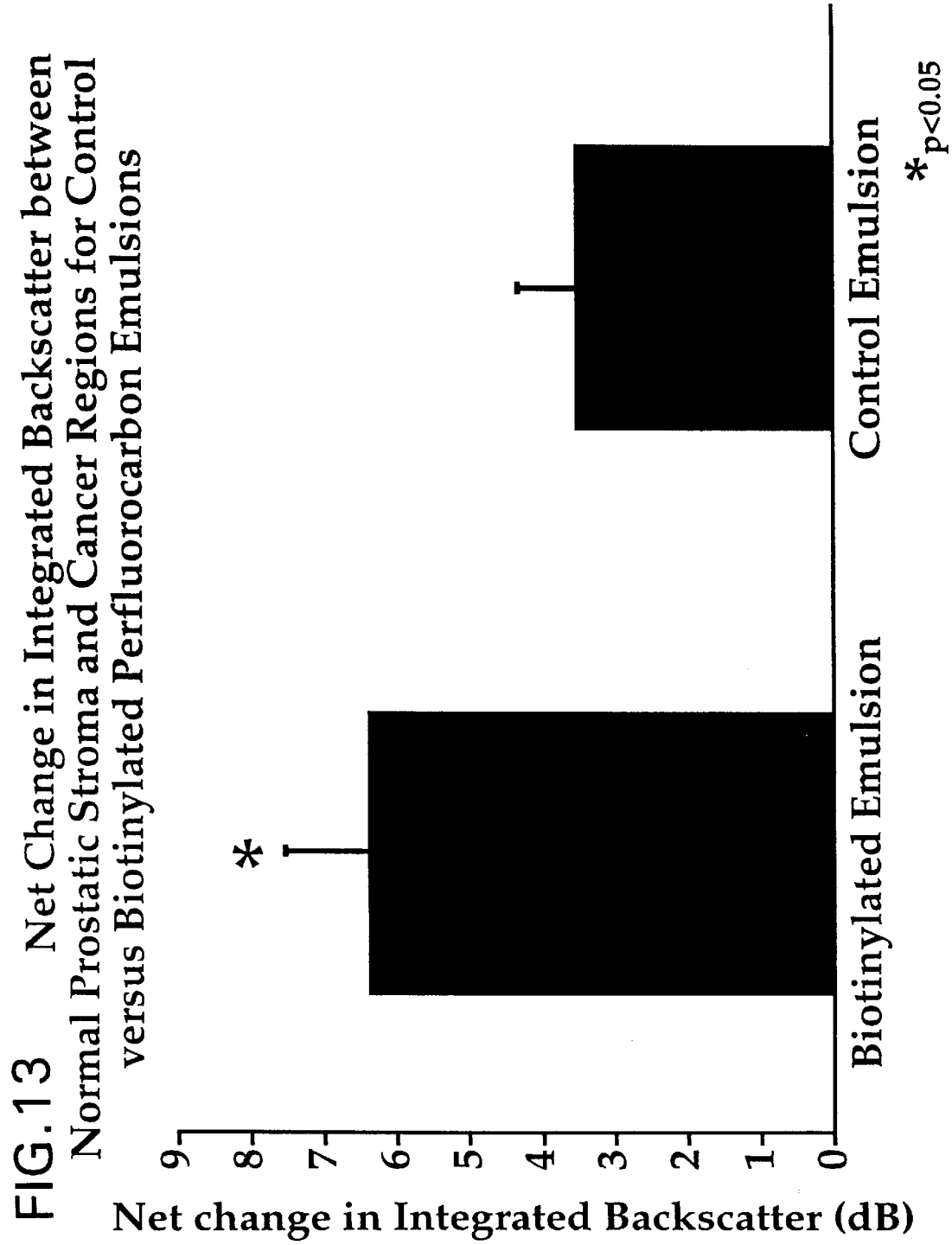
FIG. 13 Net Change in Integrated Backscatter between Normal Prostatic Stroma and Cancer Regions for Control versus Biotinylated Perfluorocarbon Emulsions

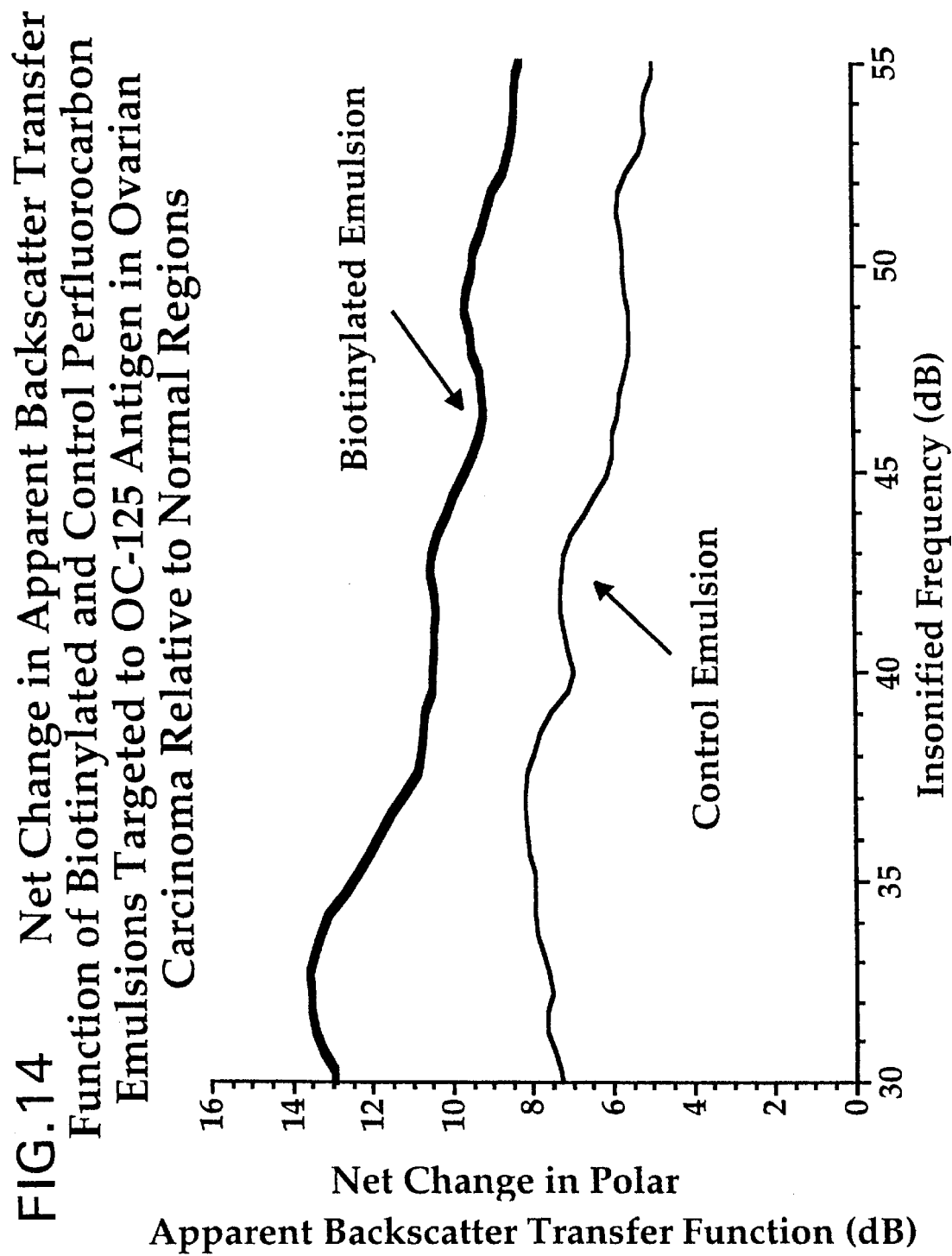
FIG. 14 Net Change in Apparent Backscatter Transfer Function of Biotinylated and Control Perfluorocarbon Emulsions Targeted to OC-125 Antigen in Ovarian Carcinoma Relative to Normal Regions

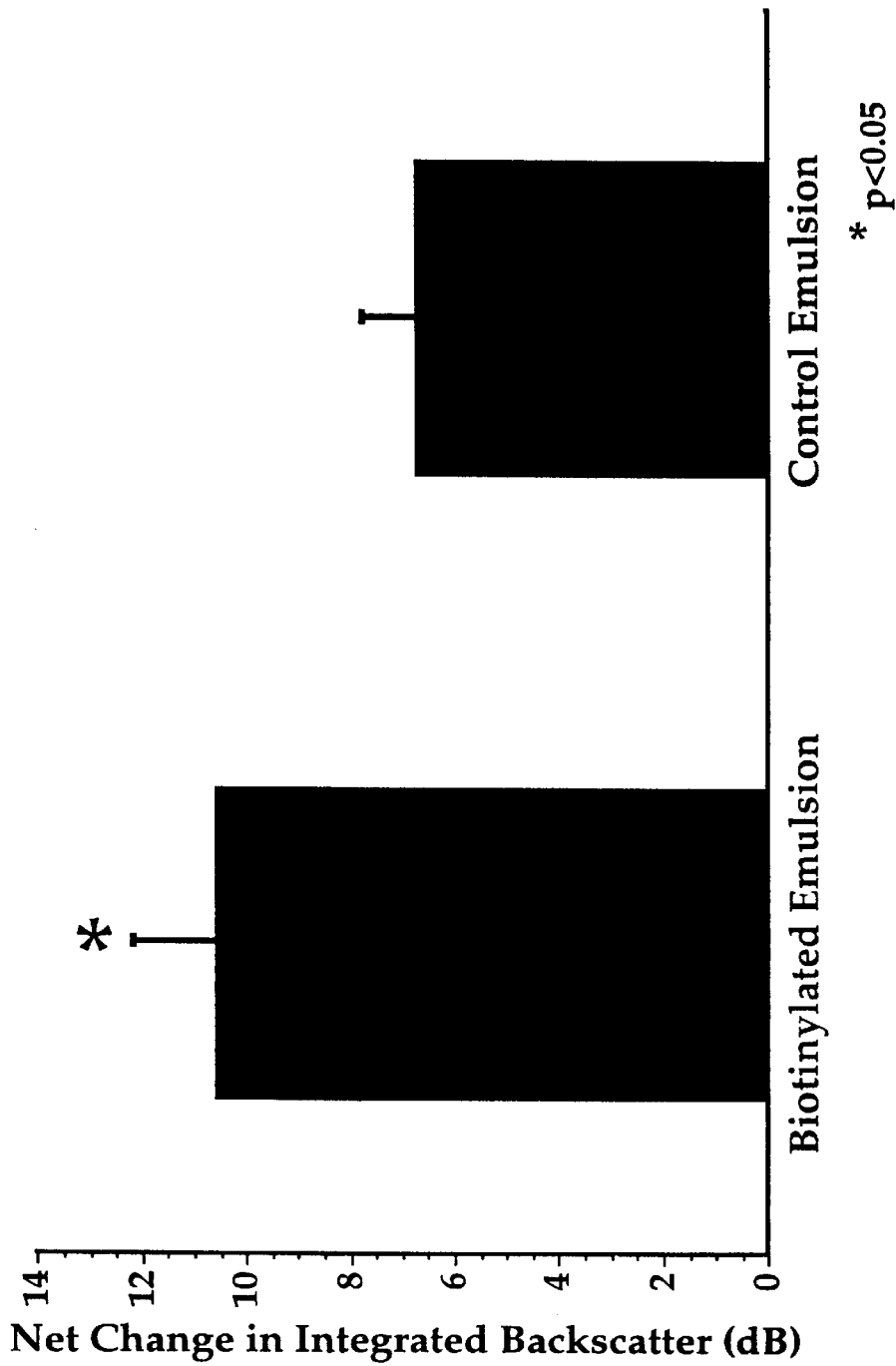
FIG. 15  Net Change in Integrated Backscatter Between Normal Ovarian Tissue and Carcinoma Regions for Control versus Biotinylated Perfluorocarbon Emulsions FIG. 16 ULTRASONIC AND OPTICAL IMAGES OF TONSIL USING PERFLUOROCARBON CONTRAST AND HORSERADISH PEROXIBASE TARGETED TO EPITHELIUM WITH ANTICYTOKERATIN ANTIBODIES
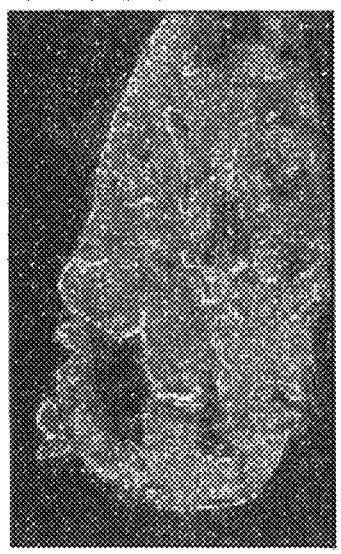
PEAK DETECTED IMAGE
100 μm SIZE
IMMUNOSTAINED TONSIL FIG. 17 PEAK DETECTED ULTRASONIC IMAGES OF TONSIL EPITHELIUM ACOUSTICALLY ENHANCED WITH ANTICYTOKERATIN ANTIBODY TARGETED PERFLUOROCARBON EMULSION
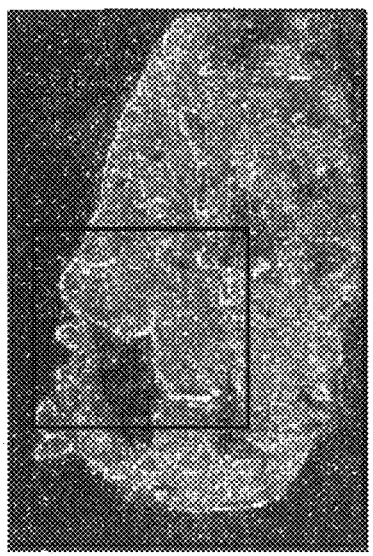
PEAK DETECTED IMAGE
100 μ STEP SIZE
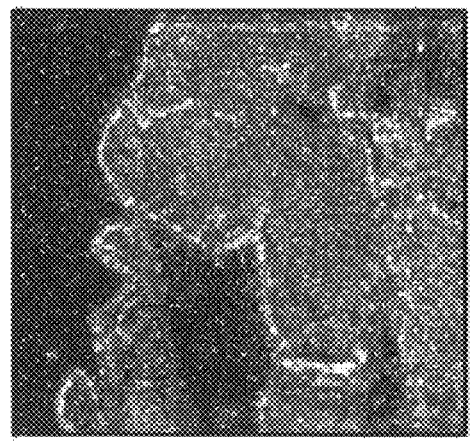
ZOOM = 50 μ STEP SIZE

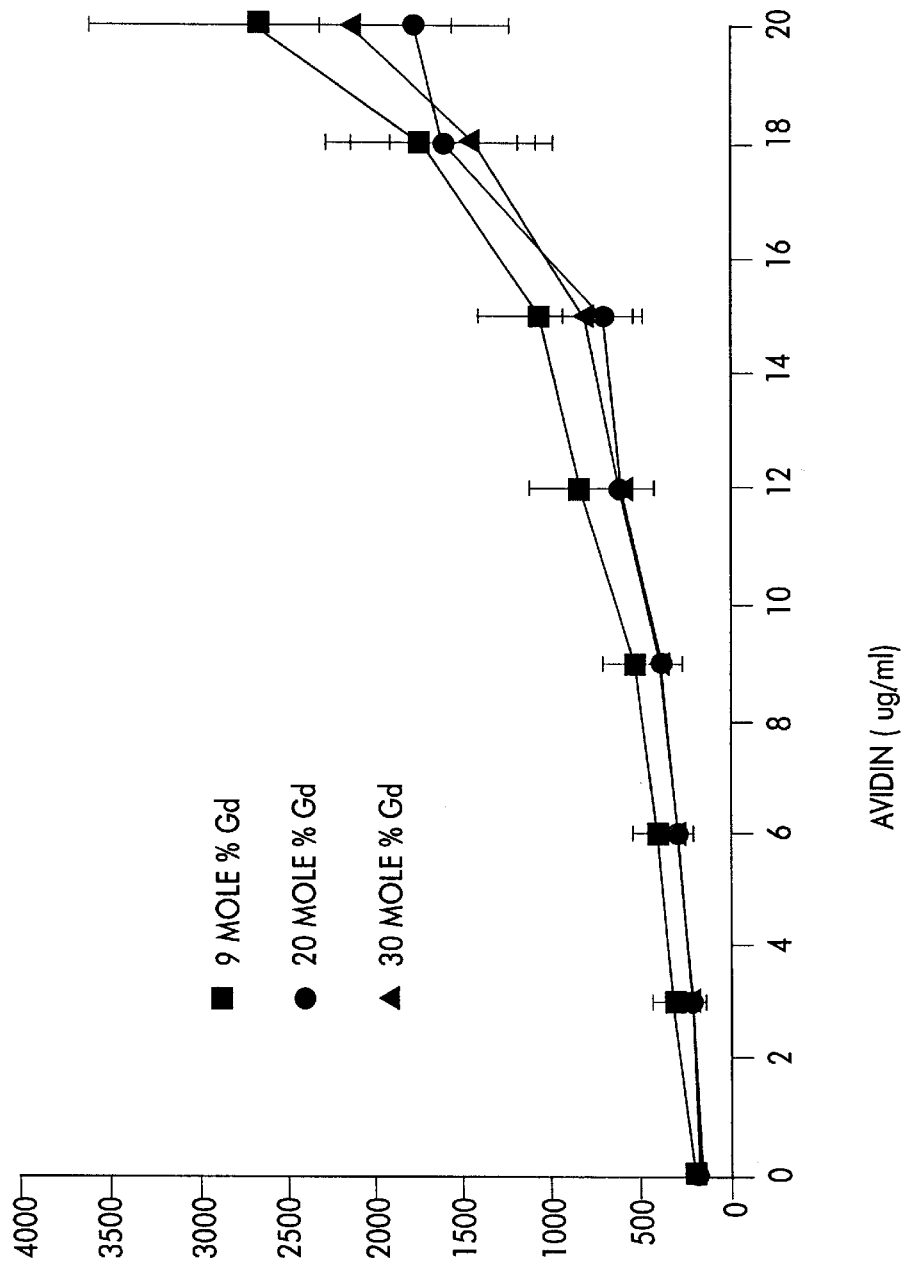

ENHANCEMENT OF THE ACOUSTIC REFLECTIVITY OF PLASMA CLOTS TREATED WITH TARGETED PERFLUOROCARBON DUAL ULTRASONIC AND MRI CONTRAST

SITE SPECIFIC BINDING SYSTEM, NUCLEAR IMAGING COMPOSITIONS AND METHODS

CROSS-REFERENCE TO RELATED APPLICATION

This application is a continuation-in-part of application Ser. No. 08/647,277, filed May 23, 1996, now U.S. Pat. No. 5,780,010, which is a continuation-in-part of application Ser. No. 08/488,743, filed Jun. 8, 1995, now U.S. Pat. No. 5,690,907 dated Nov. 25, 1997.

BACKGROUND OF THE INVENTION

This invention relates to a novel site specific binding system and novel compositions, and more particularly, to such a system and compositions which are useful in improved methods for ultrasonic imaging, drug or chemotherapeutic agent delivery, and diagnostic assays and detection systems.

Heretofore, with respect to ultrasonic imaging, although ultrasonic contrast agents based upon "bubble" technology have been demonstrated to develop an acoustic impedance mismatch by virtue of gas encapsulated either in protein (Feinstein et al., J. Am. Coll. Cardiol. 1990; 16:316–324 and Keller et al., J. Am. Soc. Echo. 1989; 2:48–52), polysaccharide (Corday et al., J. Am. Coll. Cardiol. 1984; 3:978–85) biodegradable polymers (Schneider et al., Invest. Radiol., 1993; 27:134–139 and Bichon et al., European Patent Application No. 890810367.4: 1990) or lipids (D'Arrigo et al., J. Neurormag., 1991; 1:134–139; Simon et al., Invest. Radiol., 1992; 27:29–34; and Unger et al., Radiology 1992; 195:453–456), no experimental evidence of site-specific targeting of an acoustic contrast or imaging agent with resultant changes in the acoustic properties of the targeted tissue, surface or support are known. This lack of results has occurred despite numerous methods described in the literature for modifying such agents for targeting purposes, and the failure of past targeting approaches may be due to the chemical nature of the agents, production process limitations or particle instabilities.

Nongaseous acoustic contrast agents have been described including lipid emulsions (Fink etp al., Ultrason. Imaging, 1985 7:191–197) liposomes (Lanza et al., J. Am. Coll. Cardiol., 1992 (abstract); 19 (3 Suppl A) 114A), and perfluorocarbon emulsions (Mattrey et al., Radiology 1982; 145: 759–762 and Mattrey et al., Ultrasound Med. 1983; 2:173–176). As with the contrast agents discussed above, no demonstration of site targeted emulsion or liposome has been reported. Again, such failure may reflect instability of the particles, process incompatibilities or the chemical nature of the contrast agent. Lipid emulsions were evaluated by Fink et al. supia and did not exhibit adequate echogenicity in studies examining hepatic imaging. A unique chemical formulation of liposomes described by Lanza et al. supra was suggested to have the potential to be a targetable ultrasonic contrast but such has not been demonstrated to date. Perfluorocarbon emulsions, Perflubron (perfluorooctylbromide, P100) and Flusol (perfluorodecalin and perfluorotripropylamine, F20) have been used as ultrasonic contrast agents and have been reported to accumulate in liver, spleen and tumors secondary to phagocytic uptake of emulsion particles at these sites (Mattrey et al. 1983, supra). These perfluorocarbon emulsions have also been noted to enhance Doppler signals and opacify lumens. Fluorocarbons and fluorocarbon emulsions for use as contrast agents are disclosed in U.S. Pat. Nos. 4,927,623, 5,077,036, 4,838,274, 5,068,098, 5,114,703, 5,362,477, 5,362,478, 5,171,755, 5,304,325, 5,350,571 and 5,403,575. However, no demonstration of perfluorocarbon emulsions as a ligand targeted acoustic contrast system has been reported.

Previous descriptions of tissue or organ targeting in biomedical ultrasonics has referred to the collection of acoustically reflective particles within or around structural tissue abnormalities. Localized acoustic enhancement of tissue pathologies (e.g. malignancies) has not been ligand-directed but rather has depended upon differential dynamic rates of particle uptake and/or clearance between normal and malignant tissues. Such contrast agents have included aqueous solutions (Ophir et al., Ultrason. Imaging 1979, 1:265–279; Ophir et al., Ultrasound Med. Biol. 1989, 15:319–333; and Tyler et al., Ultrason. Imaging, 3:323–329), emulsions (Fink et al. Ultrason. Imaging, 1985, 7:191–197), and suspensions (Mattrey et al. 1982 supra and Mattrey et al., Radiology, 1987, 163:339–343). Although the possibility of ligand-directed ultrasonic contrast targeting with acoustically reflective liposomes has been suggested, no successful applications of this concept have been reported (Lanza et al. 1992, supra and Valentini et al., J. Am. Coll. Cardiol., 1995, 25:16A). Previous approaches to targeting in vivo of particles have involved direct conjugation of a ligand (e.g. monoclonal antibody) to a vesicle by a variety of methods (see, for example, Torchlin et al., Biochem. Biophys. Res. Commun. 1978, 85:983–990; Endoh et al., J. Immunol. Methods, 1981, 44:79–85; Hashimoto et al., J. Immunol. Methods, 1983, 62:155–162 and Martin et al., Biochemistry, 1981, 20:4229–4238).

There remains a need for new and improved methodologies for ligand-based binding systems which can be adapted as an ultrasonic contrast system permitting detection of molecular moieties such as peptides, carbohydrates or nucleic acids and whose uses can range from ultrasound-based ELISA-like laboratory diagnostic assays in liquid and solid phase systems and in cell cultures; electrophoretic, chromatographic and hybridization detection systems to the detection of thrombi, infections, cancers and infarctions in patients with the use of conventional ultrasonic imaging methods.

SUMMARY OF THE INVENTION

Among the several objects of the invention may be noted the provision of a novel method for ligand-based binding of lipid encapsulated particles to molecular epitopes on a surface in vivo or in vitro, the provision of such a method in which the ligand is conjugated to the lipid encapsulated particles through an avidin-biotin interaction and the resulting conjugate is bound to molecular epitopes on a surface; the provision of such a method which is useful for enhancing the acoustic reflectivity of a biological surface for ultrasonic imaging; the provision of a method of this type wherein the conjugate formed is effective for imaging by x-ray, ultrasound, magnetic resonance or positron emission tomography; the provision of compositions for use in ultrasonic imaging of a biological surface and for enhancing the acoustic reflectivity of such a surface; the provision of ultrasonic contrast agents which become highly reflective when bound to the desired site or biological surface through the ligand-based binding system of the invention; and the provision of such methods and compositions which are capable of targeting and altering the echogenic properties of a tissue surface for improved and specific identification of pathological processes. Other objects will be in part apparent and in part pointed out hereinafter.

Briefly, in its broadest embodiment, the present invention is directed to a method for ligand-based binding of lipid encapsulated particles to molecular epitopes on a surface in vivo or in vitro which comprises sequentially administering (a) a site-specific ligand activated with a biotin activating agent; (b) an avidin activating agent; and (c) lipid encapsulated particles activated with a biotin activating agent, whereby the ligand is conjugated to the particles through an avidin-biotin interaction and the resulting conjugate is bound to the molecular epitopes on such surface. The conjugate is effective for imaging by x-ray, ultrasound, magnetic resonance or positron emission tomography. In a more specific embodiment, the invention is directed to a method for enhancing the acoustic reflectivity of a biological surface through the sequential administration of the above-noted components whereby the resulting conjugate is bound to a natural or synthetic surface to enhance the acoustic reflectivity thereof for ultrasonic imaging. The invention is also directed to compositions for use in ultrasonic imaging of such surfaces and for enhancing the acoustic reflectivity thereof.

BRIEF DESCRIPTION OF THE DRAWINGS

FIG. 9 shows ultrasonic images of plasma thrombi before and after exposure to control or biotinylated emulsions;

FIG. 11 shows ultrasonic images of femoral artery thrombus acoustically enhanced with biotinylated perfluorocarbon emulsion in vivo;

FIG. 12 is a graph showing the net change in apparent backscatter transfer function of biotinylated and control perfluorocarbon emulsions targeted to prostate specific antigen in prostatic carcinoma relative to normal regions;

FIG. 13 is a graph showing the net change in integrated backscatter between normal prostatic stroma and cancer regions for control versus biotinylated perfluorocarbon emulsions;

FIG. 14 is a graph showing the net change in apparent backscatter transfer function of biotinylated and control perfluorocarbon emulsions targeted to OC-125 antigen in ovarian carcinoma relative to normal regions;

FIG. 15 is a graph showing the net change in integrated backscatter between normal ovarian tissue and carcinoma regions for control versus biotinylated perfluorocarbon emulsions;

FIG. 16 shows ultrasonic and optical images of tonsil using perfluorocarbon contrast and horseradish peroxidase targeted to epithelium with anticytokeratin antibodies;

FIG. 17 shows peak detected ultrasonic images of tonsil epithelium acoustically enhanced with anticytokeratin antibody targeted perfluorocarbon emulsion.

FIG. 18 is a graph showing avidin titration curves for three biotinylated perfluorocarbon emulsions incorporating varying concentrations of gadolinium-DTPA-BOA;

DESCRIPTION OF THE PREFERRED EMBODIMENTS

Figure 1:
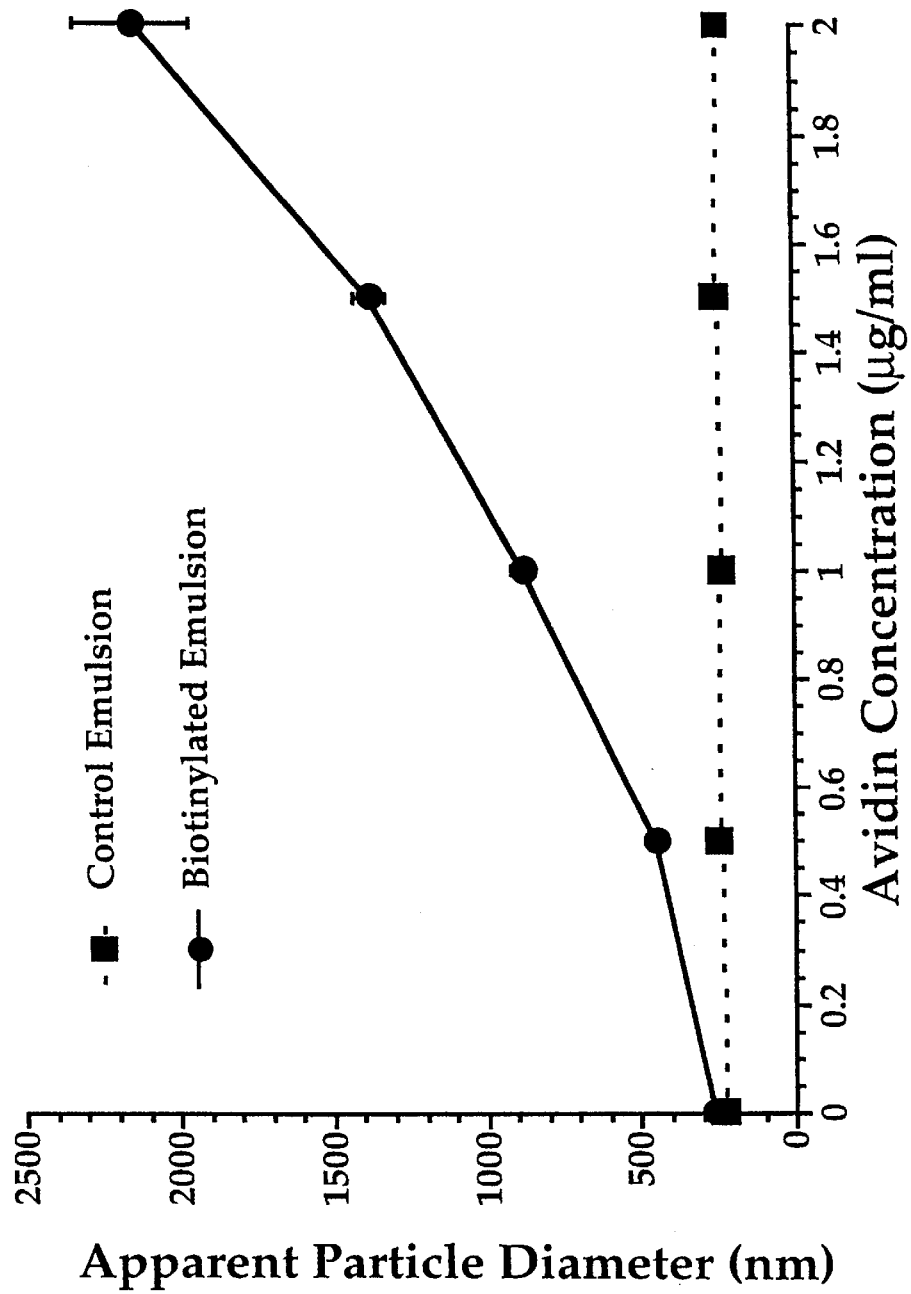
FIG. 1 is a graph showing changes in aggregate particle size of biotinylated and control perfluorocarbon emulsions with increasing avidin concentration.

In accordance with the present invention, it has now been found that a ligand-based binding system having broad application may be achieved through ligand-based binding of lipid encapsulated particles to molecular epitopes on a surface in vivo or in vitro by sequentially administering (a) a site-specific ligand activated with a biotin activating agent; (b) an avidin activating agent; and (c) lipid encapsulated particles activated with a biotin activating agent, whereby the ligand is conjugated to the lipid encapsulated particles through an avidin-biotin interaction or complexing and the resulting conjugate is bound to the molecular epitopes on the surface. The ligand-based binding system of the present invention thus permits detection of molecular moieties such as peptides, carbohydrates or nucleic acids with a specific ligand probe (e.g. an antibody or antibody fragment) complexed or conjugated with avidin and biotin, the latter being carried by lipid encapsulated particles (e.g. biotinylated lipid encapsulated emulsion or liposome). The ligand-based binding system of the invention may be employed in an ultrasonic contrast agent system, ultrasound-based ELISA-like laboratory diagnostic assays in liquid and solid phase systems and in cell cultures, electrophoretic, chromatographic and hybridization detection systems, and for the detection of thrombi, infections, cancers and infarctions in patients with the use of conventional ultrasonic imaging methods. The invention may also be applied for therapeutic purposes by delivery of chemotherapeutic agents or drugs to desired sites due to the specificity of the binding system coupled with the ability to monitor the progress of the therapeutic treatment through repeated imaging at such sites. In this regard, the above-referred to conjugate of the ligand to the lipid encapsulated particles through an avidin-biotin interaction or complexing is effective for imaging by x-ray, ultrasound, magnetic resonance or positron emission tomography.

In one embodiment of the invention, there is provided a method for enhancing the reflectivity of a biological surface by sequentially administering to the surface (a) a site-specific ligand activated with a biotin activating agent; (b) an avidin activating agent; and (c) lipid encapsulated particles activated with a biotin activating agent; whereby the ligand is conjugated to the lipid encapsulated particles through an avidin-biotin interaction and the resulting conjugate is bound to the biological surface to enhance the acoustic reflectivity thereof for ultrasonic imaging. This novel triphasic approach utilizes an avidin-biotin interaction to permit administration of the targeting ligand separate from the acoustic lipid encapsulated particles. In a specific application of the method in accordance with the invention, a biotinylated ligand is first systemically administered to a patient to pretarget the tissue or biological surface of interest and to circulate for a period of time necessary or sufficient to optimize the percentage bound. In the second phase, avidin is administered, circulates and binds to the biotinylated ligand attached to the target tissue or surface and to any residual, free circulating ligand. Avidin cross-linking increases the avidity and stability of the ligand on the target tissue or surface while promoting the rapid clearance of circulating avidin-ligand complexes via the reticuloendothelial system. In the third phase, the biotinylated lipid encapsulated particles are administered, binding to avidin through unoccupied biotin binding sites, and imparting increased acoustic contrast to the targeted tissue surface. Repeated sequential administration of avidin and the biotinylated lipid encapsulated particles may be carried out to amplify the acoustic contrast effect of the lipid encapsulated particles bound to the targeted surface.

In the practice of the invention, the ligand employed may be, for example, constituted by monoclonal or polyclonal antibodies, viruses, chemotherapeutic agents, receptor agonists and antagonists, antibody fragments, lectin, albumin, peptides, hormones, amino sugars, lipids, fatty acids, nucleic acids and cells prepared or isolated from natural or synthetic sources. In short, any site-specific ligand for any molecular epitope or receptor to be detected through the practice of the invention may be utilized.

The ligand is activated with a biotin activating agent. As employed herein, the term "biotin activating agent" or "biotinylated" encompasses biotin, biocytin and other biotin analogs such as biotin amido caproate N-hydroxysuccinimide ester, biotin 4-amidobenzoic acid, biotinamide caproyl hydrazide and other biotin derivatives and conjugates. Other derivatives include biotin-dextran, biotin-disulfide-N-hydroxysuccinimide ester, biotin-6 amido quinoline, biotin hydrazide, d-biotin-N hydroxysuccinimide ester, biotin maleimide, d-biotin p-nitrophenyl ester, biotinylated nucleotides and biotinylated amino acids such as Nε-biotinyl-l-lysine.

In the second phase, as previously mentioned, an avidin activating agent is administered. As employed herein, the term "avidin activating agent" or "avidinized" encompasses avidin, streptavidin and other avidin analogs such as streptavidin or avidin conjugates, highly purified and fractionated species of avidin or streptavidin, and non or partial amino acid variants, recombinant or chemically synthesized avidin analogs with amino acid or chemical substitutions which still accommodate biotin binding.

The lipid encapsulated particles or contrast agent employed in the third phase may be constituted, for example, by a biotinylated emulsion or liposome which may contain a gas, liquid or solid. In a specific example, the lipid encapsulated particles may be constituted by a perfluorocarbon emulsion, the emulsion particles having incorporated into their outer coating a biotinylated lipid compatible moiety such as a derivatized natural or synthetic phospholipid, a fatty acid, cholesterol, lipolipid, sphingomyelin, tocopherol, glucolipid, stearylamine, cardiolipin, a lipid with ether or ester linked fatty acids or a polymerized lipid. Thus, the biotinylated contrast agent constituting the lipid encapsulated particles may be produced by incorporating biotinylated phosphatidylethanolamine into the outer lipid monolayer of a perfluorocarbon emulsion.

Perfluorocarbon emulsions are particularly well suited for biomedical applications and for use in the practice of the present invention. They are known to be stable, biologically inert and readily metabolized, primarily by trans-pulmonic alveolae evaporation. Further, their small particle size easily accommodate transpulmonic passage and their circulatory half-life (4–8 hours) advantageously exceeds that of other agents. Also, perfluorocarbons have been used to date in a wide variety of biomedical applications, including use as artificial blood substitutes. For use in the present invention, various fluorocarbon emulsions may be employed including those in which the fluorocarbon is a fluorocarbon-hydrocarbon, a perfluoroalkylated ether, polyether or crown ether. Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorotributylamine, perfluorodecalin, perfluorooctylbromide, perfluorodichlorooctane, perfluorodecane, perfluorotripropylamine, perfluorotrimethylcyclohexane or other perfluorocarbon compounds. Further, mixtures of such perfluorocarbon compounds may be incorporated in the emulsions utilized in the practice of the invention. As a specific example of a perfluorocarbon emulsion useful in the invention may be mentioned a perfluorodichlorooctane emulsion wherein the lipid coating thereof contains between approximately 50 to 99.5 mole percent lecithin, preferably approximately 55 to 70 to mole percent lecithin, 0 to 50 mole percent cholesterol, preferably approximately 25 to 45 mole percent cholesterol and approximately 0.5 to 10 mole percent biotinylated phosphatidylethanolamine, preferably approximately 1 to 5 mole percent biotinylated phosphatidylethanolamine. Other phospholipids such as phosphatidylserine may be biotinylated, fatty acyl groups such as stearylamine may be conjugated to biotin, or cholesterol or other fat soluble chemicals may be biotinylated and incorporated in the lipid coating for the lipid encapsulated particles. The preparation of an exemplary biotinylated perfluorocarbon for use in the practice of the invention is described hereinafter in accordance with known procedures.

When the lipid encapsulated particles are constituted by a liposome rather than an emulsion, such a liposome may be prepared as generally described in the literature (see, for example, Kimelberg et al., CRC Crit. Rev. Toxicol. 6,25 (1978) and Yatvin et al., Medical Physics, Vol. 9, No. 2, 149 (1982)). Liposomes are known to the art and generally comprise lipid materials including lecithin and sterols, egg phosphatidyl choline, egg phosphatidic acid, cholesterol and alpha-tocopherol.

With respect to the particle size of the lipid encapsulated particles constituted by a perfluorocarbon emulsion or liposome, the particle size may range between approximately 0.05 to 5 microns and preferably between approximately 0.05 and 0.5 micron. Small size particles are thus preferred because they circulate longer and tend to be more stable than larger particles.

As indicated, the ligand is conjugated to the lipid encapsulated particles or perfluorocarbon emulsion through an avidin-biotin interaction. The ligand may also be conjugated to the emulsion directly or indirectly through intervening chemical groups or conjugated directly or indirectly to biotin or a biotin analog through intervening chemical groups such as an alkane spacer molecule or other hydrocarbon spacer. The use of spacer molecules between the ligand and biotin or between biotin and the emulsion is not required but aids in rendering the biotin more available for binding to avidin.

As previously mentioned, the emulsion or liposome constituting the lipid encapsulated particles or vesicles may contain a gas, liquid or solid. The gas may be nitrogen, oxygen, carbon dioxide or helium and may, for example, be evolved from the fluorocarbon component of the emulsions described above.

Alternatively, but less preferably, the ligand-based binding method of the invention may be carried out by sequentially administering a site-specific ligand activated with a biotin or avidin activating agent and lipid encapsulated particles activated with a biotin or avidin activating agent, a biotin activating agent being used where an avidin activating agent was employed in the first step and an avidin activating agent being used where a biotin activating agent was employed in the first step. The direct conjugation of the ligand to a perfluorocarbon emulsion, for example, is less preferable since it may accelerate in vivo clearance of the emulsion contrast agent.

In the practice of the invention, it has been unexpectedly found that the individual components of the ultrasonic contrast agents as described above are poorly reflective or have low echogenicity in the bloodstream but become highly reflective when the ligand-avidin-emulsion complex is formed in vivo at the desired site or biological surface and thereby substantially enhances the acoustic reflectivity thereof for ultrasonic imaging. This is in sharp contrast to previously known sonographic contrast agents which are inherently bright or of high reflectivity in the bloodstream. The improved acoustic reflectivity achieved through the present invention provides the advantage of enhancing the signal-to-noise ratio because the background contrast from lipid encapsulated particles in the blood is minimal. Thus, the present invention offers an improved noninvasive method for forming an acoustic contrast agent which can be targeted in vitro or in vivo and which when bound to a specific desired site alters the acoustic reflectivity of a tissue surface or support media in a manner detectable with ultrasonic transducers suitable for biomedical and diagnostic applications within a frequency range of at least 5 to 50 MHz (nominal center frequencies may be wider ranging based on the knowledge that these are broad band transducers). The method of the invention advantageously provides a practical means for detecting any molecular epitope or receptor for which a biotinylated monoclonal antibody or other ligand is available without the need for use of ionizing radiation with or without associated invasive procedures in various clinical applications and while employing standard, commercially available ultrasonic technology. The present invention does not employ ultrasonic contrast systems or agents to delineate blood flow as in the prior art but rather to detect physiologic and pathologic events by sensing the accumulation of the contrast agent at specific binding sites.

In the application of the invention to diagnostic assays such as ultrasound-based ELISA-type laboratory diagnostic assays in liquid and solid phase systems, the surface on which ligand-based binding of lipid encapsulated particles to molecular epitopes occurs may be, for example, nylon, nitrocellulose membranes or a gel as well as a biological surface.

The ligand-based binding system of the invention may also be applied to provide a chemotherapeutic agent or gene therapy delivery system combined with ultrasonic imaging. For example, chemotherapeutic agents or immune activating drugs such as tissue plasminogen activator, adriamycin, vincristine, urokinase, streptokinase, methotrexate, cytarabine, thioguanine, doxorubicin, 5-fluorouracil, cisplatin, etoposide, ifosfamide, asparginase, deoxycoformycin, hexamethyl melamine and including radioactive agents may be incorporated in the lipid encapsulated particles and become part of the conjugate bound to a specific biological surface site for therapeutic action. The present invention would also advantageously permit the site to be ultrasonically imaged in order to monitor the progress of the therapy on the site and to make desired adjustments in the dosage of therapeutic agent subsequently directed to the site. The invention thus provides a noninvasive means for the detection and therapeutic treatment of thrombi, infections, cancers and infarctions in patients while employing conventional ultrasonic imaging systems.

Further, as indicated, the invention may be applied to nuclear medicine imaging by adding a radioactive or chemical moiety to the surface and/or formulating said moiety inside the emulsion. These agents can be transported and concentrated at sites specifically targeted by the ligand where the added moiety or moieties provide additional imaging and/or therapeutic character or capability. Radionuclides such as technetium-99m ($^{99m}Tc$) and other radioactive moieties known to the art such as indium, gallium, thallium and iodine may be chelated and applied to a lipid encapsulated emulsion for nuclear imaging in accordance with the invention. Thus, for example, $^{99m}Tc$-pertechnetate has been successfully incorporated directly into an emulsion and found to have 10 fold improved $^{99m}Tc$ retention over simple aqueous injections.

Radionuclides, such as technetium-99m, are routinely attached to lipid surfaces, including red cells (Vorne et al., Clin Nucl Med 1992; 17:14–17; Suzman et al. Ann Surg 1996; 224:29–36; and Ng et al., Dis Colon Rectum, 1997; 40:471–7) and leukocytes (Mortelmans et al., J Nucl Med., 1989; 30:2022–2028; and Vinjamuri et al., Lancet., 1996; 347:233–235) for human diagnostic imaging and liposomes (Umbrain et al., Br J Anaesth., 1995; 75:311–318; and Umbrain et al., Acta Anaesthesiol Scand., 1997; 41:25–34) on a more experimental basis. The most common approaches have involved the use of stannous (II) chloride or stannous oxinate to anchor $^{99m}Tc$ to the lipid membrane (Umbrain et al., Br J Anaesth., 1995; 75:311–318). More recently, $^{99m}Tc$-hexamethyl-propyleneamineoxime ($^{99m}Tc$-HM-PAO) has gained favor as a lipophilic chelator, able to diffuse through cell membranes, and is now approved and routinely used for human cerebral tumors imaging and leukocyte/red cell tagging applications (Mortelmans et al., J Nucl Med., 1989; 30:2022–2028; and Umbrain et al., Acta Anaesthesiol Scand., 1997; 41:25–34). No investigator has to date reported conjugation or incorporation of a radionuclide such as $^{99m}Tc$ to an emulsion for ligand-targeted diagnostic imaging and/or therapeutic applications.

The following examples illustrate the practice of the invention.

EXAMPLE 1

The procedure for preparing a biotinylated lipid encapsulated perfluorodichlorooctane emulsion for use in ultrasound imaging is as follows.

The biotinylated lipid perfluorodichlorooctane (PFDCO) emulsion is comprised of the following components: PFDCO (40% v/v), safflower oil (2.0% w/v), a surfactant co-mixture (2.0% w/v) and glycerin (1.7% w/v). The surfactant co-mixture is composed of approximately 64 mole % lecithin, 35 mole % cholesterol and 1 mole % N-(6-biotinoyl)amino) hexanoyl)dipalmitoyl-L-alpha-phosatidylethanolamine. These components are weighed together into a test tube and dissolved in chloroform. The chloroform is stripped from the material and the resulting surfactant mixture is dried in a 50° C. vacuum oven overnight. The co-mixture is dispersed into water by sonication resulting in a liposome suspension. The suspension is transferred into a 30 mL capacity blender cup (Dynamics Corporation of America, New Hartford, Conn.) along with the PFDCO and oil. The mixture is blended for 30–60 seconds to a pre-emulsion. The preemulsified sample is transferred to the reservoir of a microfluidizer, model S110 (Microfluidics, Newton, Mass.), and emulsified for three minutes at 10,000 psi. To prevent the emulsion from heating excessively during homogenization, the shear valve and mixing coil of the microfluidizer are immersed in a room temperature water bath during processing. The final temperature of the emulsion is approximately 35° C. The finished emulsion is bottled in 10 mL serum vials, blanketed with nitrogen gas and sealed with stopper/crimp seal. The average particle size of the finished product, measured by a laser light scatter particle sizer (Brookhaven Instruments Corporation, Holtsville, N.Y.), is 250 nm.

EXAMPLE 2

The incorporation of biotinylated phosphatidylethanolamine into the encapsulating lipid monolayer of perfluorocarbon emulsion is prepared as described in Example one and demonstrated to increase aggregate particle size in the presence of titrated concentrations of avidin (Pierce, Rockford, Ill. 61105). An identically prepared control emulsion is prepared which incorporates nonbiotinylated phosphatidylethanolamine into the outer lipid monolayer of the perfluorocarbon emulsion. Avidin is resuspended in isotonic phosphate buffered saline (PBS, Fisher Inc., Fair Lawn, N.J.). Within a polystyrene cuvette, a 3.0 ml reaction mixture is prepared containing PBS, biotinylated or control perfluorocarbon emulsion (20 $\mu$l) and avidin, at 0.0, 0.5, 1.0, 1.5 or 2.0 $\mu$g/ml. Contents are mixed by gentle inversion and react for thirty minutes at room temperature. Emulsion particle sizes are determined in triplicate with a Brookhaven BI-90 particle size analyzer (Holtsville, N.Y.) at 37° C. Aggregate particle size of the biotinylated emulsion increased progressively from a baseline of 263±2.54 nm to greater than 2000 nm with increasing concentration of avidin (FIG. 1). Marked flocculation and sedimentation are noted when avidin concentrations exceed 2.0 $\mu$g/ml. The particle size of the control emulsion is 234±3.81 nm in diameter and addition of 2.0 $\mu$g of avidin to the reaction mixture does not affect particle size. These results clearly demonstrate that the biotinylated phosphatidylethanolamine is incorporated and oriented appropriately into the outer lipid monolayer of the perfluorocarbon emulsion and that surface biotins are adequately available to avidin in the media. Multiple biotin binding sites on the avidin molecule as well as multiple biotin residues on the surface of the emulsion progresses towards a rapid complexing of particles in vitro.

EXAMPLE 3

Figure 2:
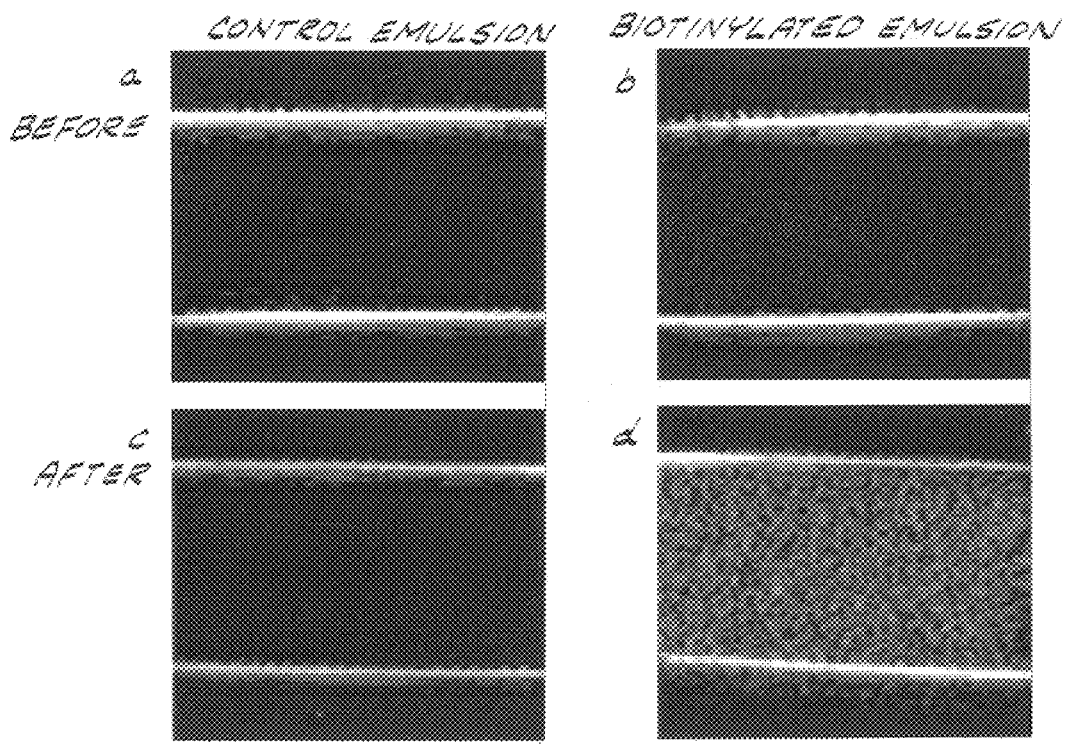
FIG. 2 shows ultrasonic images of control and biotinylated perfluorocarbon emulsion before and after the addition of avidin.
Figure 3:
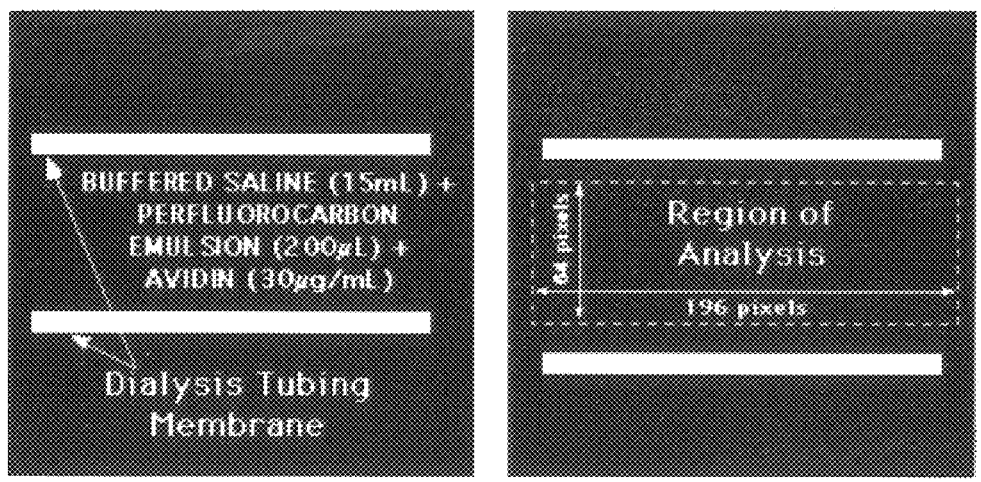
FIG. 3 is a graphic illustration of dialysis tubing images and region of interest placement for gray scale analysis.
Figure 4:
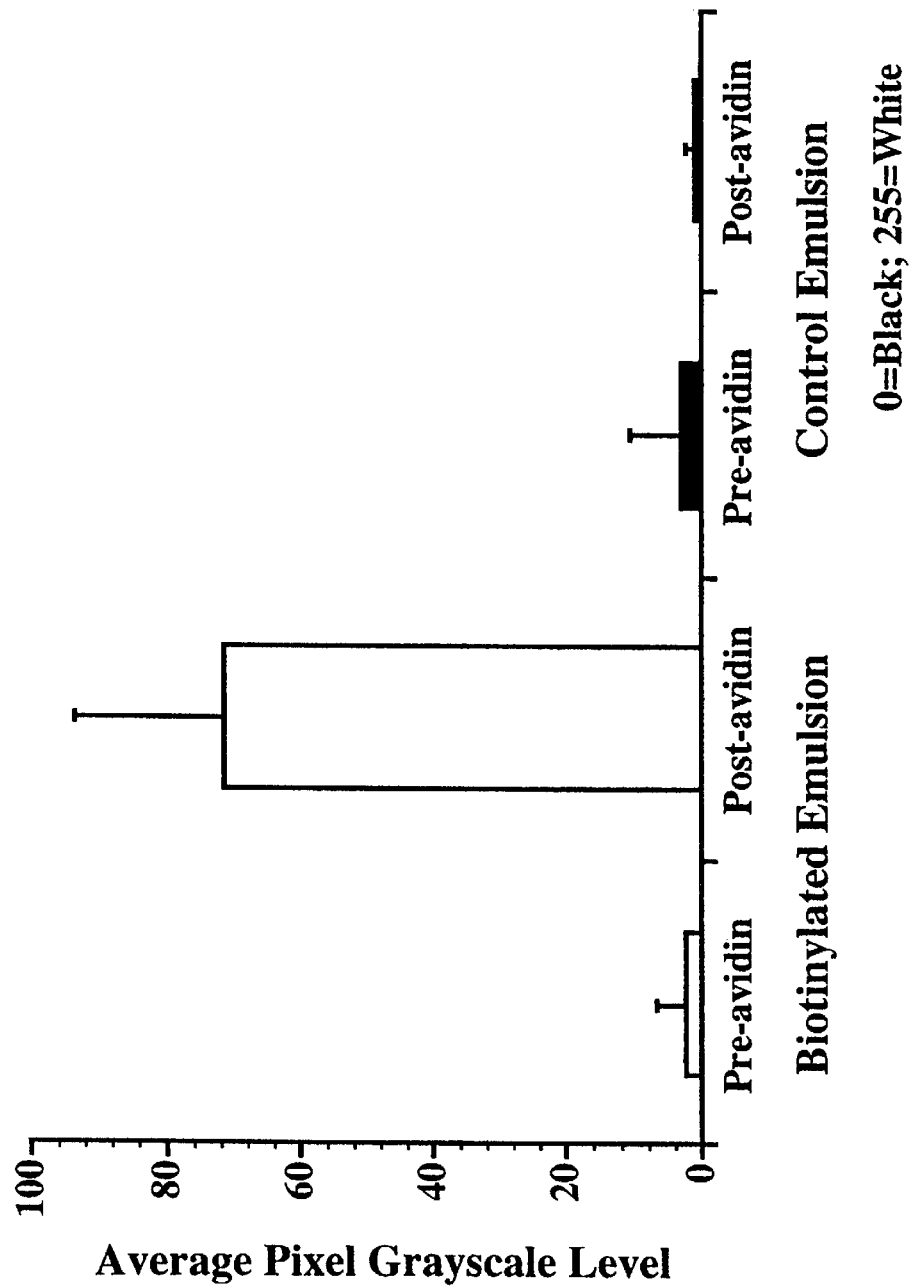
FIG. 4 is a graph showing changes in average pixel gray scale associated with the addition of avidin to control or biotinylated perfluorocarbon emulsion.

Biotinylated perfluorocarbon emulsion particles, approximately 250 nm in diameter, with low independent acoustic reflectivity, are complexed with avidin in solution which eventuates aggregation and enhances echogenicity. Biotinylated and control perfluorocarbon emulsion (200 $\mu$l) prepared as described previously are diluted in PBS (15 ml) and placed within dialysis tubing (Spectra/Por 4, 25 mm, MWCO 12,000–14,000, Spectrum Medical Industries, Inc., Los Angeles, Calif.), ultrasonically imaged within a PBS water bath at room temperature using a 7.5 MHz focused transducer and a Hewlett Packard (HP) Sonos 2500 Phased Array Imaging System (Andover, Mass.). Real-time images are recorded to SVHS video tape for subsequent image analysis. Pixel grayscale and homogeneity are assessed on selected freeze-frame images using NIH Image 1.47 (National Institutes of Health). Avidin (30 $\mu$g/ml) is added to each emulsion suspension, mixed by gentle inversion and allowed to complex for 30 minutes. The emulsion suspensions are optically opaque but ultrasonically undetected prior to the addition of avidin. Complexing of the biotinylated perfluorocarbon emulsion ensues rapidly with the addition of avidin and a white, flocculant precipitate soon appears. Avidin induces no changes in control emulsion suspension. Insonification of the suspensions reveals that the biotinylated perfluorocarbon emulsion particles opacify the dialysis tubing; whereas, the control particles are not appreciated acoustically (FIG. 2). Gray scale echo intensity analysis of freeze-frame images of the control and biotinylated emulsion suspensions before and after avidin are summarized in FIGS. 3 and 4. The increased average grayscale level of the biotinylated emulsion (71.3±22.1) suspension relative to its pre-avidin pixel gray scale level (2.2±4.4) demonstrates the acoustic enhancement achieved. Average pixel gray scale levels of the control emulsion before (3±7.33) and after (1.0±1.3) avidin addition are similar. These results demonstrate the low acoustic reflectivity of the perfluorocarbon emulsion when imaged as independent particles in comparison with the enhanced echogenic nature of the aggregated biotinylated particles. The lack of acoustic change in the control emulsion suspension in the presence of avidin confirms the ligand specificity of the biotinylated emulsion.

EXAMPLE 4

Biotinylated perfluorocarbon emulsion, approximately 250 nm diameter, are specifically targeted to avidin, covalently bound to a modified nitrocellulose membrane and increases the acoustic reflectivity of the membrane surface at high ultrasonic frequencies (30 to 60 MHz). Briefly, nitrocellulose membranes (S+S NC™, Schleicher & Schuell, Keane, N.H.) were conjugated to avidin using a diaminohexane (Sigma Chemical Co., St. Louis, Mo.) spacer and glutaraldehyde (Sigma Chemical Co., St. Louis, Mo.) activation as described by Másson et al. (Electrophoresis 1993, 14, 860–865). Nitrocellulose discs (2 cm diameter) are soaked in 2.5% diaminohexane dissolved in deionized water for 60 minutes with constant slow rotary agitation. Membranes are washed with 1M acetic acid for 6–7 hours followed by an 18+ hour deionized water wash with constant agitation. The membranes are placed in 1% glutaraldehyde in 0.1M sodium bicarbonate buffer, pH 10.0 for 15 minutes then washed for three hours with deionized water. Nitrocellulose membranes are stored and dried at 4° C. until use; storage does not exceed three days.

Fifty (50) $\mu$l of avidin (250 $\mu$g) are spotted dropwise upon the center of six membranes with a microliter syringe and allowed to dry. Each membrane is extensively washed with a 0.1% Tween-20 (Sigma Chemical Co., St. Louis, Mo.) in PBS then placed in 3% bovine serum albumin (BSA, crystallized, Sigma Chemical Company, St. Louis, Mo.) dissolved in PBS-0.1% Tween-20 for 20 minutes to blockade nonspecific protein binding sites around the periphery of the disc. After the BSA blockade, each disc is extensively washed with PBS and placed in 300 $\mu$l of either biotinylated or control perfluorocarbon emulsion suspended in 4 ml PBS for 20 minutes. Unbound emulsion is removed in serial PBS washes. Each disc is reexposed to avidin and control or biotinylated emulsion to ensure saturated coverage of the nitrocellulose surface. The nitrocellulose discs are washed and stored in PBS at 4° C. until imaged with acoustic microscopy.

For acoustic microscopic imaging, each nitrocellulose disc is placed flat above a polished stainless steel plate in a polystyrene holder with a 2×2 cm central window removed. The mounted specimen is immersed into PBS at ambient temperature for ultrasonic insonification. A custom designed acoustic microscope, utilizing a 50 MHz (nominal frequency) broadband, focused, piezoelectric delay-line transducer (¼ inch diameter, ½ inch focal length, Model V390, Panametrics Co., Waltham, Mass.) operated in the pulse-echo mode is utilized for insonification. Backscattered radio frequency (RF) data is collected and digitized at 500 megasamples per second utilizing a Tektronix DSA 601 digitizing oscilloscope (Beaverton, Oreg.) with 8-bit resolution. A variable gain system is used to increase the effective dynamic range of this digitizer. Radio frequency data are acquired from approximately 100 independent sites from each region of interest with 100 micron lateral step resolution.

A radio frequency peak-detected scan of the data is converted into a gray scale (0=lowest scattering, 255= highest scattering) map to allow selection of regions of interest for integrated backscatter analysis. Radio frequency (RF) ultrasonic data are stored in a raster scan format and analyzed with custom software. Segments of the RF lines are gated for integrated backscatter analysis to encompass the front and back surfaces of the nitrocellulose disc. The data are multiplied by a rectangular window and their power spectra are determined by fast-Fourier transformation. The power spectra from the specimens referenced to the power spectrum returned from a near-perfect steel planar reflector and the frequency-dependent backscatter transfer function across the useful bandwidth of the transducer (30 to 60 MHz) are computed and expressed in decibels relative to acoustic scattering from the near perfect steel plate reflector (Wong et al., Ultrasound in Med & Biol. 1993; 19: 365–374). Integrated backscatter (IB) is computed as the average of the frequency-dependent backscatter transfer function across the useful bandwidth of the transducer.

Figure 5:
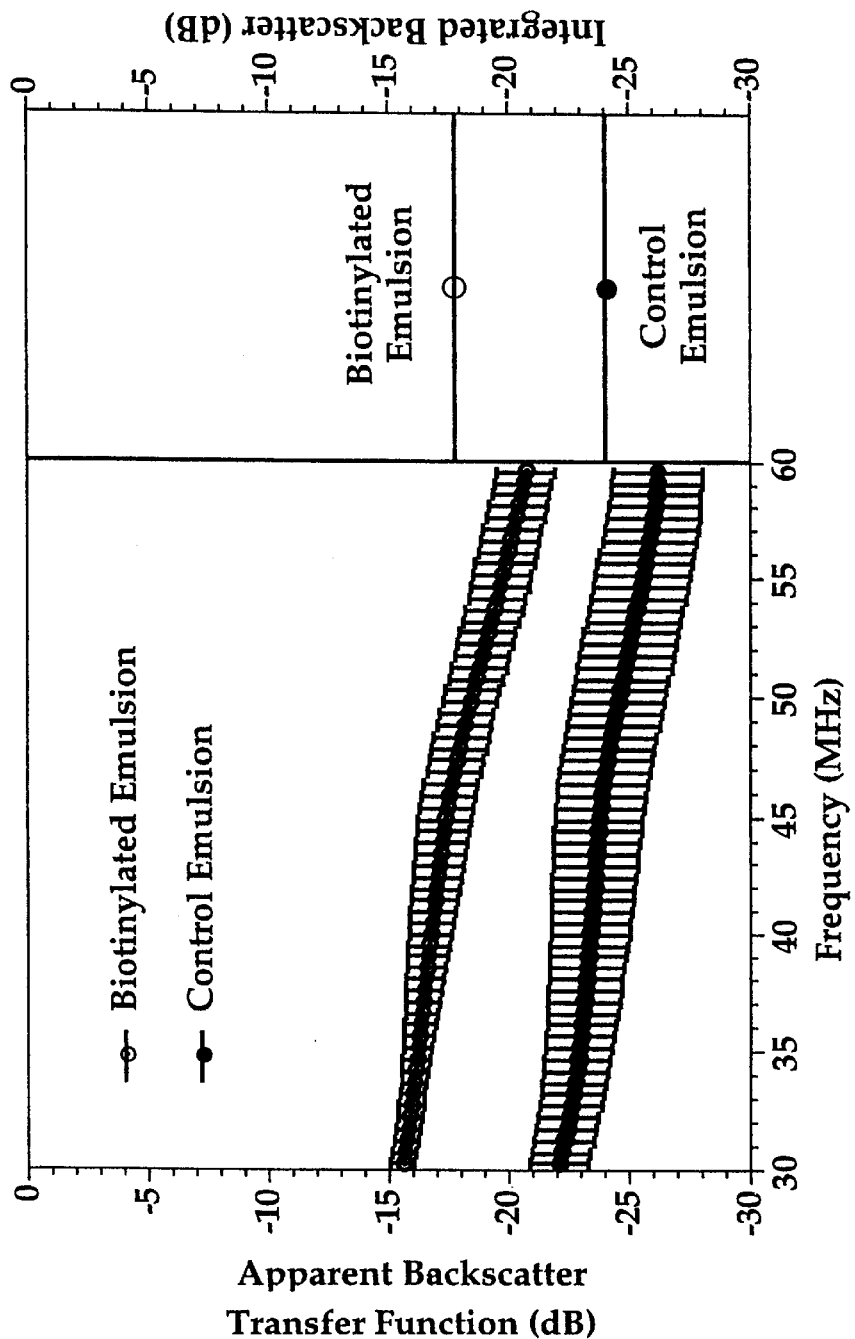
FIG. 5 is a graph showing the effect of control and biotinylated perfluorocarbon emulsion on apparent backscatter transfer function and integrated backscatter of avidinized nitrocellulose membranes.

Discs incubated with biotinylated perfluorocarbon emulsion have central regions with high acoustic scattering in comparison with the peripheral (i.e. background) regions of the same disc. Nitrocellulose discs incubated with the control emulsion have no central high scattering regions and no differences in acoustic character is detected by changes in the RF signature between the central and peripheral regions of the disc. IB from the centrally-located, biotinylated emulsion region (−17.8±0.2 db) is 6.3±0.1 dB(4-fold) greater (p<0.05) than IB from the analogous region on the control disc (−24.1±0.2 dB). The frequency-dependent variation in apparent backscatter transfer function (mean±SEM) from the avidin spotted regions of the biotinylated and control emulsion discs are presented in FIG. 5. A smooth and consistently greater acoustic response is noted across the frequency spectrum due to the bound biotinylated emulsion. These results demonstrate the effectiveness of the biotinylated perfluorocarbon emulsion to specifically target a surface bound antigen and dramatically alter the acoustic reflectivity of the surface with the bathing medium, increasing the ultrasonic backscattered power at high frequencies.

EXAMPLE 5

Biotinylated perfluorocarbon emulsion (250 nm diameter) is specifically targeted to D-dimer covalently attached to a modified nitrocellulose membrane utilizing a biotinylated anti-D-dimer $F_{(ab)}$ fragment-avidin complex and results in a marked increase in the acoustic power reflected from the surface. D-dimer is covalently linked to nitrocellulose discs modified with a diaminohexane spacer arm and activated with glutaraldehyde as previously described in Example 4. Fifty (50) $\mu$g of D-dimer is spotted with a microliter syringe upon the center of three of six membranes and allowed to air dry. Unbound D-dimer is exhaustively washed from the membranes with phosphate buffered saline (PBS)-0.1% Tween-20. Nonspecific protein binding sites of all membranes are blocked with 3% bovine serum albumin (BSA) in PBS-0.1% Tween-20 for 20 minutes followed by serial PBS washes. D-dimer spotted membranes are incubated with 12.5 $\mu$g biotinylated anti-D-dimer $F_{(ab)}$ antibody in 4.0 ml 3% BSA for 2 hours, washed with PBS buffer and then incubated with 250 $\mu$g avidin in 4 ml PBS for 30 min. After removing unbound avidin with PBS washes, the discs are exposed to either biotinylated or control perfluorocarbon emulsion (300 $\mu$l) in 4.0 ml PBS for 20 minutes. Excess emulsion is removed with PBS buffer washes. Discs are reexposed to avidin and perfluorocarbon emulsion as described above and the membranes are stored in PBS at 4° C. until imaging.

For acoustic microscopic imaging, each nitrocellulose disc is placed flat above a polished stainless steel plate in a polystyrene holder, immersed in PBS at ambient temperature, and insonified with a custom designed acoustic microscope, utilizing a 50 MHz (nominal frequency) broadband, focused, piezoelectric delay-line transducer (¼ inch diameter, ½ inch focal length, Model V390, Panametrics Co., Waltham, Mass.) operated in the pulse-echo mode. Backscattered radio frequency (RF) data is collected and digitized at 500 megasamples per second utilizing a Tektronix DSA 601 digitizing oscilloscope (Beaverton, Oreg.) with 8-bit resolution. A variable gain system is used to increase the effective dynamic range of this digitizer. Radio frequency data are acquired from approximately 100 independent sites from each region of interest with 100 micron lateral step resolution.

A radio frequency peak-detected scan of the data is converted into a gray scale (0=lowest scattering, 255= highest scattering) map of the disc to allow visual inspection and selection of regions of interest for integrated backscatter (IB) analysis. Radio frequency (RF) ultrasonic data are stored in a raster scan format and analyzed with custom software. Segments of the RF lines are gated for integrated backscatter analysis to encompass the front and back surfaces of the nitrocellulose disc. The data are multiplied by a rectangular window and their power spectra are determined by fast-Fourier transformation. The power spectra from the specimens referenced to the power spectrum returned from a near-perfect steel planar reflector and the frequency-dependent backscatter transfer function across the useful bandwidth of the transducer (30 to 60 MHz) are computed and expressed in decibels relative to acoustic scattering from the near perfect steel plate reflector (Wong et al., Ultrasound in Med & Biol. 1993; 19: 365–374). Integrated backscatter is computed as the average of the frequency-dependent backscatter transfer function across the useful bandwidth of the transducer.

Figure 6:
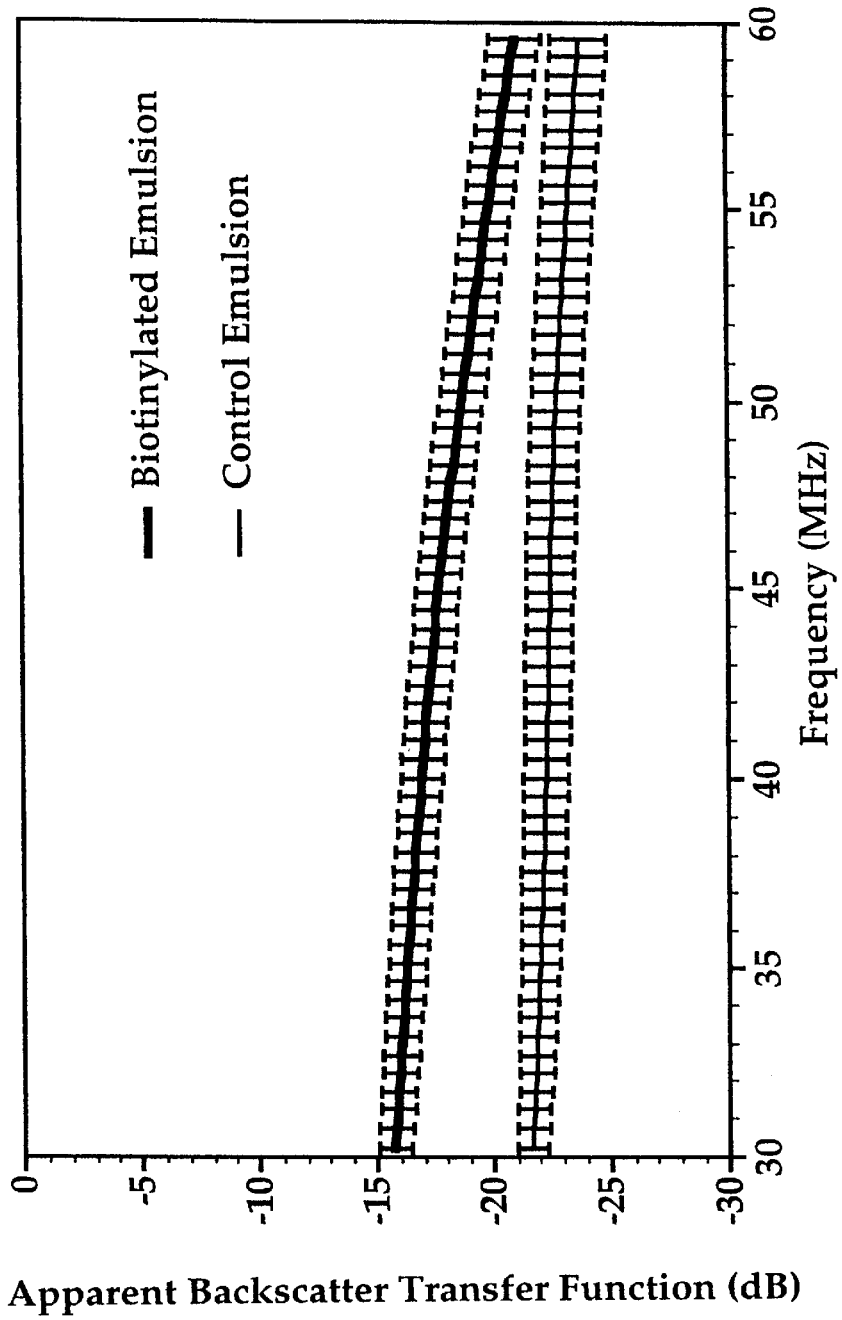
FIG. 6 is a graph showing the apparent backscatter transfer function of biotinylated and control perfluorocarbon emulsions targeted to D-dimer covalently conjugated to nitrocellulose membranes.
Figure 7:
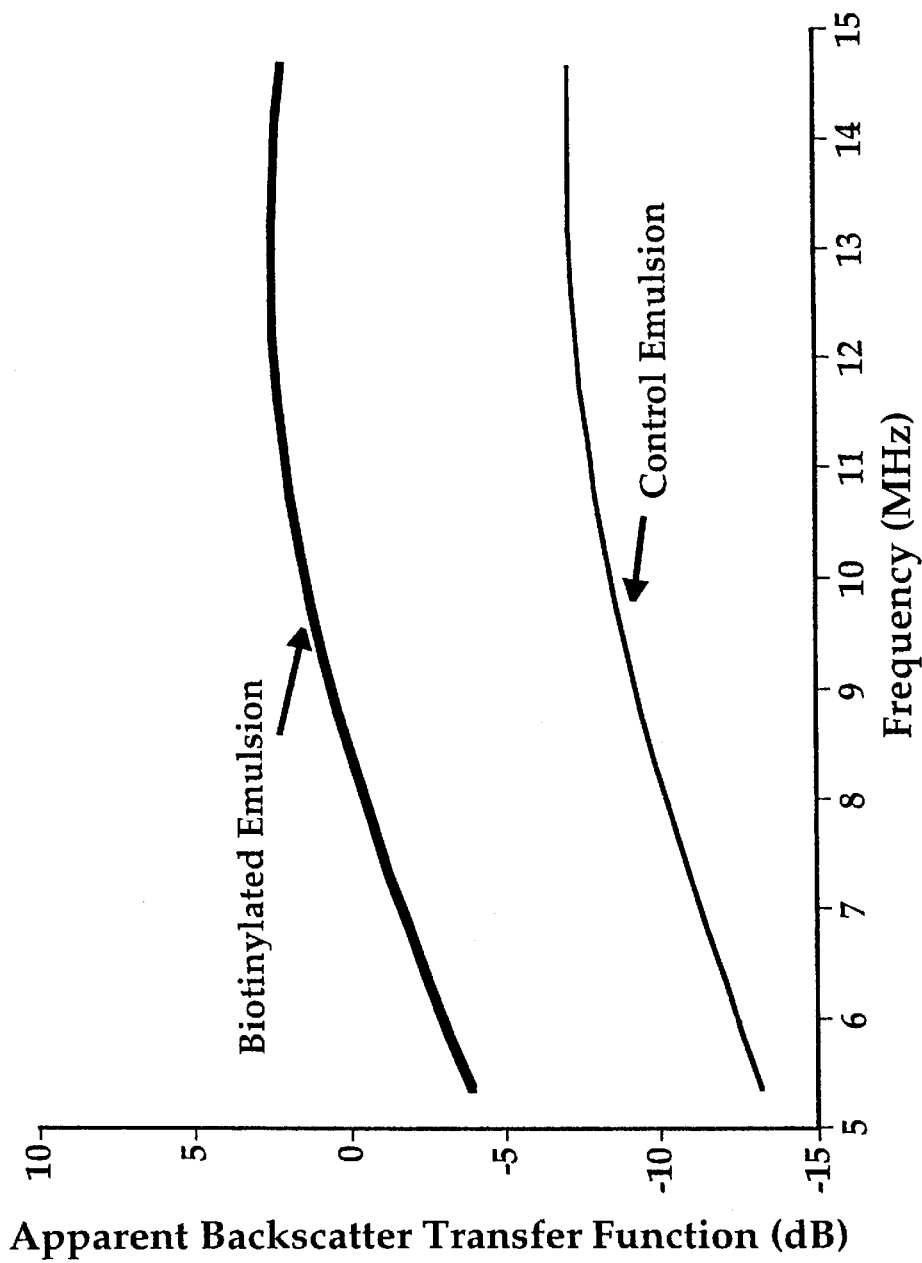
FIG. 7 is a graph showing the apparent backscatter transfer function (dB) of biotinylated and control perfluorocarbon emulsions at low ultrasonic frequencies.
Figure 8:
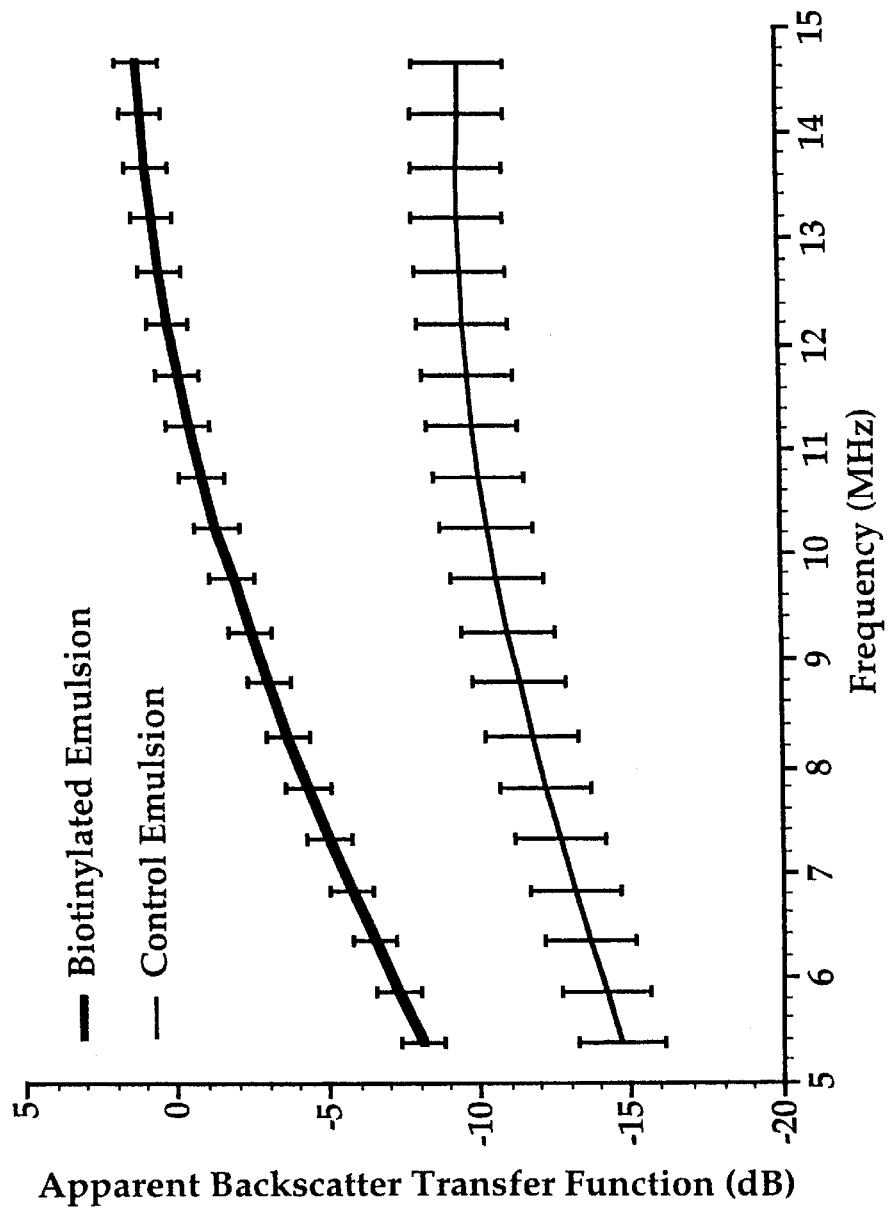
FIG. 8 is a graph showing the apparent backscatter transfer function of biotinylated and control perfluorocarbon large particle size emulsions targeted to avidinized nitrocellulose membranes.
Figure 10:
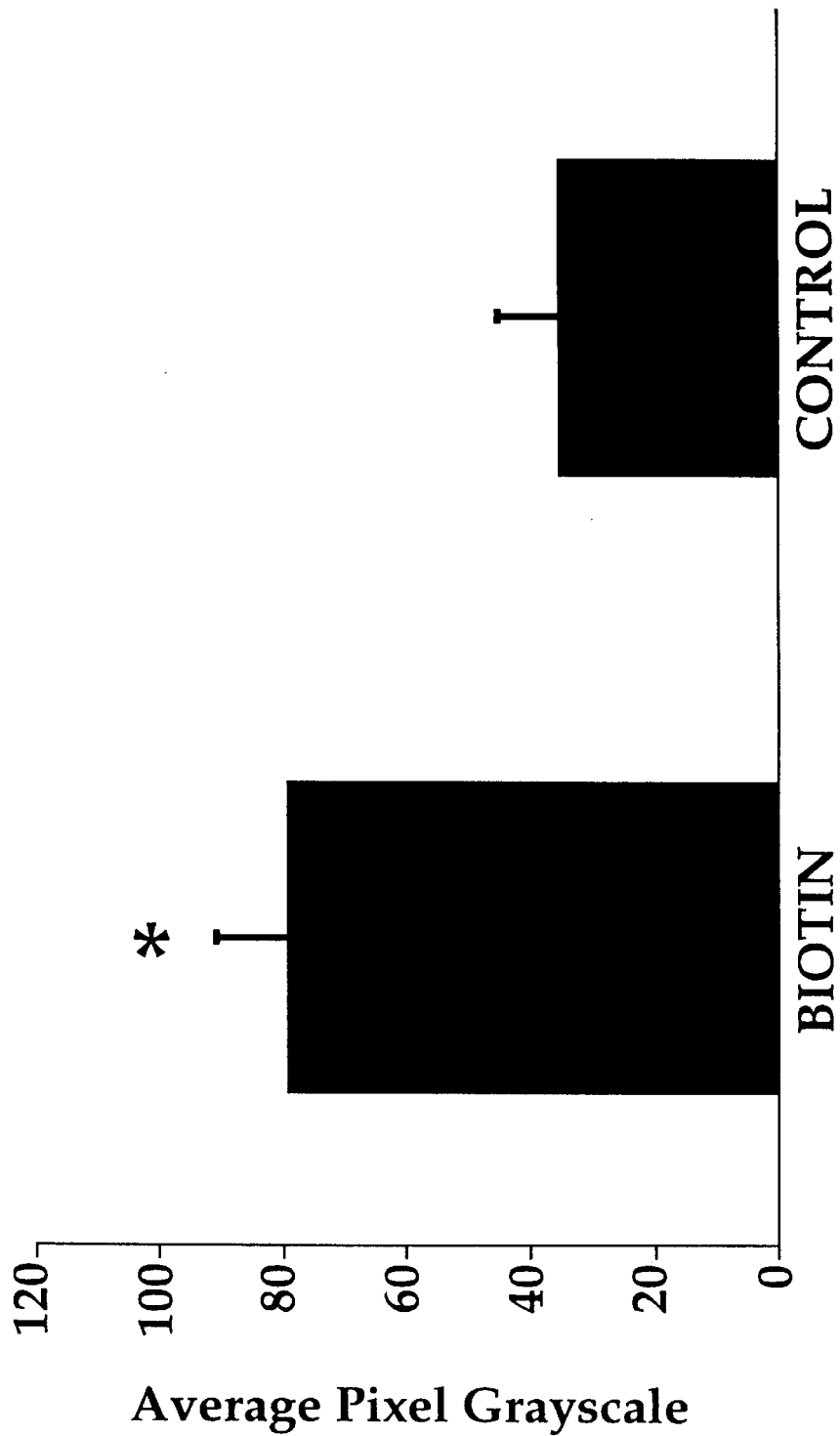
FIG. 10 is a graph showing the average pixel grayscale level of plasma thrombi pre-targeted with antifibrin monoclonal antibody and exposed to control or biotinylated perfluorocarbon emulsion.

Biotinylated, anti-D-dimer $F_{(ab)}$ fragment is specifically bound to the central region of the D-dimer spotted discs and crosslinked by avidin through its biotin moiety. As in previous examples, biotinylated perfluorocarbon emulsion specifically binds to the antibody bound avidin; whereas, the nonspecific binding of the control emulsion have no binding and are not detected acoustically. IB of the biotinylated emulsion coated nitrocellulose (−18.0±0.2 dB) was greater by 4.6±0.1 dB (p<0.05) than that from the control disc (−22.6±0.1 dB) over the 30 to 60 MHz frequency range. The frequency-dependent variation in apparent backscatter transfer function (mean+SEM) of the biotinylated and control emulsion discs are presented in FIG. 6. A smooth and consistently greater acoustic response is noted across the frequency spectrum due to the bound biotinylated emulsion. These data confirm and extend the findings of Example 4 with avidin alone, demonstrating that biotinylated perfluorocarbon emulsion bound through a specific, targeting ligand system can significantly enhance the acoustic backscatter of a solid support surface.

EXAMPLE 6

Biotinylated perfluorocarbon emulsion (250 nm diameter) is specifically targeted to avidin conjugated to nitrocellulose discs and insonified at clinically relevant frequencies (5 to 15 MHz) and significantly increases the acoustic backscatter of the membrane. Briefly, nitrocellulose membranes (S+S NC™, Schleicher & Schuell, Keane, N.H.) are conjugated to avidin using a diaminohexane (Sigma Chemical Co., St. Louis, Mo.) spacer and glutaraldehyde (Sigma Chemical Co., St. Louis, Mo.) activation as described by Masson et al. (Electrophoresis 1993, 14, 860–865). Nitrocellulose discs (2 cm diameter) are soaked in 2.5% diaminohexane dissolved in deionized water for 60 minutes with constant, slow rotary agitation. Membranes are transferred to and washed with 1M acetic acid for 6–7 hours then transferred for continued washing in deionized water for at least 18 additional hours with constant agitation. The membranes are placed in 1% glutaraldehyde in 0.1M sodium bicarbonate buffer, pH 10.0 for 15 minutes. After glutaraldehyde activation is complete, the membranes are washed with continued agitation for three hours. The nitrocellulose membranes stored and dried at 4° C. until use; storage does not exceed three days.

Fifty (50) μl of avidin (250 μg) are spotted dropwise upon the center of a nitrocellulose membrane with a microliter syringe and allowed to dry. Each membrane is washed with 0.1% Tween-20 (Sigma Chemical Co., St. Louis, Mo.) in phosphate buffered saline (PBS) then placed in 3% bovine serum albumin (BSA, crystallized, Sigma Chemical Company, St. Louis, Mo.) dissolved PBS-0.1% Tween-20 for 20 minutes to blockade nonspecific protein binding sites around the periphery of the disc. After the BSA blockade, each disc is washed with PBS and placed in 300 μl of either biotinylated or control perfluorocarbon emulsions suspended in 4 ml PBS for 20 minutes with mild, rotary agitation. The unbound emulsion is removed with washes of PBS. Each disc is reexposed to avidin, washed with PBS, reexposed to control or biotinylated perfluorocarbon emulsion and rewashed with PBS as previously described. The nitrocellulose discs are stored in PBS at 4° C. until imaged with the acoustic microscope.

For acoustic microscopic imaging, each nitrocellulose disc is placed flat above a polished stainless steel plate in a polystyrene holder with a 2 cm×2 cm central window removed. The mounted specimen is immersed into PBS at ambient temperature for ultrasonic insonification. A custom designed acoustic microscope, utilizing a 10 MHz (nominal frequency) broadband, focused, piezoelectric delay-line transducer (½ inch diameter, 2 inch focal length, Model V311, Panametrics Co., Waltham, Mass.) operated in the pulse-echo mode is utilized for insonification. Backscattered radio frequency (RF) data is collected and digitized at 500 megasamples per second utilizing a Tektronix DSA 601 digitizing oscilloscope (Beaverton, Oreg.) with 8-bit resolution. A variable gain system is used to increase the effective dynamic range of this digitizer. Radio frequency data are acquired from approximately 100 independent sites from each region of interest with 250 micron lateral step resolution.

A radio frequency peak-detected scan of the data is converted into a gray scale (0=lowest scattering, 255=highest scattering) map of the disc to allow visual inspection and selection of regions of interest for integrated backscatter analysis. Radio frequency ultrasonic data are stored in a raster scan format and analyzed with custom software. Segments of the RF lines are gated for integrated backscatter analysis to encompass the front and back surfaces of the nitrocellulose disc. The data are multiplied by a rectangular window and their power spectra are determined by fast-Fourier transformation. The power spectra from the specimens referenced to the power spectrum returned from a near-perfect steel planar reflector and the frequency-dependent backscatter transfer function across the useful bandwidth of the transducer (5 to 15 MHz) are computed and expressed in decibels relative to acoustic scattering from the near perfect steel plate reflector (Wong et al., Ultrasound in Med & Biol. 1993; 19: 365–374). Integrated backscatter (IB) is computed as the average of the frequency-dependent backscatter transfer function across the useful bandwidth of the transducer.

Discs incubated with biotinylated perfluorocarbon emulsion have central regions with high acoustic scattering relative to the peripheral regions of the same disc or the central regions of the control emulsion disc. Nitrocellulose discs incubated with the control emulsion have no high scattering regions. IB of the biotinylated emulsion coated nitrocellulose (0.5±0.5 dB) was greater by 9.6±0.1 dB (8-fold) ($p<0.05$) than that from the control disc (−9.2±0.5 dB) over the 5 to 15 MHz frequency range. The frequency-dependent variation in apparent backscatter transfer function (mean±SEM) of the biotinylated and control emulsion discs are presented in FIG. 7. A smooth and consistently greater acoustic response is noted across the frequency spectrum due to the bound biotinylated emulsion. These data confirm and extend the findings of Examples 4 and 5 with avidin and D-dimer, demonstrating that biotinylated perfluorocarbon emulsion bound through a specific, targeting ligand system can significantly enhance the acoustic backscatter of a solid support surface and that this improved acoustic backscatter is detected at low, clinically useful ultrasonic frequencies (5 to 15 MHz) as well as high frequencies (30 to 60 MHz).

EXAMPLE 7

Biotinylated perfluorocarbon contrast, approximately 3000 nm diameter, is specifically targeted to avidin conjugated to nitrocellulose discs and insonified at clinically relevant frequencies (at least 5 to 15 MHz bandinidth). Briefly, nitrocellulose membranes (S+S NC™, Schleicher & Schuell, Keane, N.H.) are conjugated to avidin using a diaminohexane (Sigma Chemical Co., St. Louis, Mo.) spacer and glutaraldehyde (Sigma Chemical Co., St. Louis, Mo.) activation as described by Masson et al. (Electrophoresis 1993, 14, 860–865). Nitrocellulose discs (2 cm diameter) are soaked in 2.5% diaminohexane dissolved in deionized water for 60 minutes with constant, slow rotary agitation. Membranes are transferred to and washed with 1M acetic acid for 6–7 hours then transferred for continued washing in deionized water for at least 18 additional hours with constant agitation. The membranes are placed in 1% glutaraldehyde in 0.1M sodium bicarbonate buffer, pH 10.0 for 15 minutes. After glutaraldehyde activation is complete, the membranes are washed with continued agitation for three hours. The nitrocellulose membranes stored and dried at 4° C. until use; storage does not exceed three days.

Fifty (50) μl of avidin (250 μg) are spotted dropwise upon the center of two of four membranes with a microliter syringe and allowed to dry. Each membrane is washed with 0.1% Tween-20 (Sigma Chemical Co., St. Louis, Mo.) in phosphate buffered saline (PBS) then placed in 3% bovine serum albumin (BSA, crystallized, Sigma Chemical Company, St. Louis, Mo.) dissolved PBS-0.1% Tween-20 for 20 minutes to blockade nonspecific protein binding sites around the periphery of the disc. After the BSA blockade, each disc is washed with PBS and placed in 300 μl of either biotinylated or control perfluorocarbon emulsions, approximately 3000 nm particle size, suspended in 4 ml PBS for 20 minutes with mild, rotary agitation. The unbound emulsion is removed with washes of PBS. Each disc is reexposed to avidin, washed with PBS, exposed to perfluorocarbon emulsion and rewashed with PBS as previously described. The nitrocellulose discs are stored in PBS at 4° C. until imaged with the acoustic microscope.

For acoustic microscope imaging, each nitrocellulose disc is placed flat above a polished stainless steel plate in a polystyrene holder with a 2 cm×2 cm central window removed. The mounted specimen is immersed into PBS at ambient temperature for ultrasonic insonification. A custom designed acoustic microscope, utilizing a broadband 10 MHz (nominal frequency) focused, piezoelectric delay-line transducer (½ inch diameter, 2 inch focal length, Model V311, Panametrics Co., Waltham, AM) operated in the pulse-echo mode is utilized for insonification. Backscattered radio frequency (RF) data is collected and digitized at 500 megasamples per second utilizing a Tektronic DSA 601 digitizing oscilloscope (Beaverton, Oreg.) with 8-bit resolution. A variable gain system is used to increase the effective dynamic range of this digitizer. Radio frequency data are acquired from approximately 100 independent sites from each region of interest with 250 micron lateral step resolution.

A radio frequency peak-detected scan of the data is converted into a gray scale (0=lowest scattering, 255= highest scattering) map of the disc to allow visual inspection and selection of regions of interest for integrated backscatter analysis. Radio frequency ultrasonic data are stored in a raster scan format and analyzed with custom software. Segments of the RF lines are gated for integrated backscatter (IB) analysis to encompass the front and back surfaces of the nitrocellulose disc. The data are multiplied by a rectangular window and their power spectra are determined by fast-Fourier transformation. The power spectra from the specimens referenced to the power spectrum returned from a near-perfect steel planar reflector and the frequency-dependent backscatter transfer function across the useful bandwidth of the transducer (5 to 15 MHz) are computed and expressed in decibels relative to acoustic scattering from the near perfect steel plate reflector (Wong et al., Ultrasound in Med & Biol. 1993; 19: 365–374). Integrated backscatter is computed as the average of the frequency-dependent backscatter transfer function across the useful bandwidth of the transducer.

Discs incubated with biotinylated perfluorocarbon emulsion have central regions with high acoustic scattering relative to the peripheral regions of the same disc and central regions of the control disc. Nitrocellulose discs incubated with the control emulsion have no central high scattering regions and no differences in acoustic character are detected between the central and peripheral regions of the disc. ID of the biotinylated emulsion coated nitrocellulose (−2.4±0.7 dB) was greater by 8.8±0.3 dB (approximately 8-fold ($p<0.05$)) than that from the control disc (−11.2±0.4 dB) over the 5 to 15 MHz frequency range. The frequency-dependent variation in apparent backscatter transfer function (mean±SEM) of the biotinylated and control emulsion discs are presented in FIG. 8. A smooth and consistently greater acoustic response is noted across the frequency spectrum due to the bound biotinylated emulsion. These data confirm and extend the findings of Examples 4, 5 and 6 with avidin and D-dimer, demonstrating that biotinylated perfluorocarbon emulsions with large particle sizes can be bound through a specific, targeting ligand system and significantly enhance the acoustic backscatter of a solid support surface. This improved acoustic backscatter is detected at clinically relevant ultrasonic frequencies, 5 to 15 MHz.

EXAMPLE 8

Biotinylated perfluorocarbon emulsion is targeted to a plasma thrombi using biotinylated antifibrin monoclonal antibodies (NIB1H10; Tymkewycz et al. 1993. Blood Coagulation and Fibrinolysis 4:211–221) and avidin. In a representative study (1 of 5), whole porcine blood is obtained and anticoagulated (9:1, v/v) with sterile sodium citrate. Blood is centrifuged at 1500 RPM at room temperature and the plasma fraction is obtained and stored at 4° C. Two porcine plasma thrombi are produced by combining plasma, 100 mM calcium chloride (3:1 v/v) and 2–5 U thrombin in a plastic tube through which 5–0 Vicryl suture is passed. Thrombi are allowed to coagulate at room temperature.

One thrombus is incubated with 150 μg antifibrin monoclonal antibody in 10 ml PBS with 1% bovine serum albumin (BSA) for two hours and a second control thrombus is incubated in PBS with 1% BSA. The antibody treated thrombus is then incubated with 0.5 mg avidin in 10 ml PBS with 1% BSA for 30 minutes. The control thrombus remains in PBS with 1% BSA. Both thrombi are washed extensively with PBS. Each thrombus is incubated with 300 μl/10 ml PBS of either biotinylated or control emulsion for 30 minutes. All thrombi are reexposed to emulsion twice to ensure uniform coverage and ultrasonically insonified (FIG. 9). Ultrasonic imaging is performed using a 7.5 MHz focused, linear phased array transducer and a Hewlett Packard Sonos 2500 Imaging System (Hewlett Packard, Inc., Andover, Mass.). All ultrasonic recordings are produced with fixed gain, compensation and time-gain compensation levels and are recorded on to SVHS videotape for subsequent image analysis. Average pixel grayscale over an extensive region of interest was sampled for 21 independent freeze-frame images for each thrombus using NIH Image 1.47 (National Institutes of Health; FIG. 10). The biotinylated perfluorocarbon emulsion is found to provide a marked acoustic enhancement of the surface. Average pixel grayscale levels of the biotinylated emulsion thrombus are 79.5±2.5 whereas the brightness of the control was markedly less (34.8±2.2, $p<0.05$). These results demonstrate the ability of biotinylated perfluorocarbon emulsion to target and acoustically enhance a biological tissue (i.e. thrombus) in vitro.

EXAMPLE 9

Biotinylated perfluorocarbon emulsion is targeted via biotinylated antifibrin antibodies (NIB5F3 and NIB1H10 Tymkewycz et al. 1993. Blood Coagulation and Fibrinolysis 4:211–221) to an isolated femoral artery thrombus in six mongrel dogs. A mongrel dog is anesthetized with sodium pentobarbital induction and halothane anesthesia. The right femoral artery and all branches are isolated at the level of the saphenous branch. A silver plated copper wire attached to a 22 ga. right angled needle point, insulated with plastic tubing (polyethylene P-240), is inserted into the femoral artery and secured with 4–0 Prolene suture. A current of 200–400 μA is applied for up to two hours. Thrombus formation is monitored with continuous wave doppler and discontinued after an approximately 50% increase in circulation velocity is noted distal to the electrical injury. Adventitial discoloration secondary to the current is appreciated proximal to the entry point of the wire. A 20 ga. catheter is inserted into a proximal branch of the femoral artery and secured with 4–0 silk suture. A pressurized 0.9% NaCl drip is attached through a three-way stopcock to the catheter. Blood flow into the isolated segment is disrupted by proximal snare ligature. Excess blood is flushed from the arterial segment to inhibit further thrombus formation by infusion of saline for 15 minutes. The distal draining branches of the femoral artery are ligated or snared with suture. Biotinylated antifibrin monoclonal antibody (50 μg/1.0 ml PBS) is injected via the catheter and flushed with a few drops of saline. The antibody is allowed to incubate for one hour then the snare ligature distal to the wire insertion is released and excess antibody is flushed through with saline for five minutes. The distal femoral artery is reoccluded and avidin (250 μg/1.0 ml PBS) is infused and incubates for 30 minutes. The distal ligature is again released and excess avidin is flushed through with saline for five minutes. The distal ligature is reestablished and biotinylated perfluorocarbon emulsion is infused and incubates for 30 minutes. After the initial exposure of the thrombus to the emulsion, the unbound emulsion is washed through with saline. Thrombi are each exposed to avidin and biotinylated perfluorocarbon emulsion as described above. In three animals, the contra lateral artery is also isolated, partially occluded with electrically induced thrombi and exposed to a control perfluorocarbon emulsion analagous to the administration of biotinylated emulsion described above. Femoral arteries exposed to either control or biotinylated perfluorocarbon emulsion are ultrasonically imaged at 7.5 MHz with a focused, linear phased array transducer and a clinical Hewlett-Packard Sonos 2500 Ultrasonic Imaging System before and after contrast administration. Acutely formed thrombi, both control and contrast targeted, are not ultrasonically appreciated. For 6 of 6 femoral arteries, partially occlusive thrombi are markedly enhanced using the antifibrin targeted biotinylated perfluorocarbon contrast. In 3 of 3 femoral arteries thrombi, exposure to the control perfluorocarbon emulsion does not accentuate their acoustic reflectivity and these thrombi remain ultrasonically undetectable. FIG. 11 reveals a representative example of a femoral artery site of thrombus formation after electrical induction before and after exposure to antifibrin antibody and biotinylated contrast. In the pre-contrast image, the femoral artery is observed with a bright echogenic wire point anode protruding into the lumen but no thrombus is appreciated. After treatment with the biotinylated contrast emulsion, a large partially occluded thrombus is clearly noted by the enhanced acoustic reflectivity (FIG. 11). Again, no thrombus is appreciated in the control artery before or after exposure to control emulsion. These results demonstrate the concept of using bound perfluorocarbon emulsion to acoustically enhance biological surfaces, such as thrombotic tissue, in vivo to enable detection with a commercially available ultrasound imaging system.

EXAMPLE 10

Biotinylated perfluorocarbon emulsion, approximately 250 nm diameter, is targeted to prostatic carcinoma using monoclonal antibodies specific for prostate specific antigen (PSA) and are acoustically detected using polar, high frequency, high resolution acoustic microscopy. Representative examples of human prostatic carcinoma tissues are routinely processed by immersion fixation in 10% neutral buffered formalin and embedded in paraffin. Twenty micron sections are prepared for acoustic microscopy; 5 micron sections are used for optical studies. All histologic sections are mounted on acid cleaned glass slides that have been coated with poly-L-lysine. All mounted sections are heated at 55° C. for 1 hour in an oven.

Prior to immunostaining, all sections are dewaxed in three changes of Americlear, and dehydrated in successive changes of 95% and 100% ethanol. Endogenous peroxidase activity is blocked only in sections prepared for optical studies by immersion in absolute methanol containing 0.6% (v/v) hydrogen peroxide for 30 minutes. These and all sections for acoustic microscopy are then rehydrated through graded ethanols and distilled water and placed in isotonic PBS (pH 7.4). All sections are incubated with target specific monoclonal antibodies.

Prostate sections are incubated with anti-PSA primary monoclonal antibodies per the recommendations of the vendor for 18 hours at 4° C. in moisture chambers. After primary incubation, sections are rinsed in isotonic PBS, then overlain with a polyclonal biotinyl-horse anti-mouse immunoglobin (VectaStain Elite Kits, Vector Laboratories, Burlingame, Calif.) for 1 hour at room temperature. After rinsing in PBS, a 30 micron section is prepared for acoustic microscopy. A section for light microscopy (5 micron) is incubated with avidin-biotin-peroxidase complex (VectaStain Elite Kit, Vector Lab) for 1 hour at room temperature. This section is rinsed in phosphate buffer (pH 7.6) and immersed in a solution of 3,3'-diaminobenzidine tetrahydrochloride (Sigma Chemicals, St. Louis, Mo.; 0.5 mg/ml in phosphate buffer, pH 7.6, containing 0.003% [v/v] hydrogen peroxide) for approximately ten minutes. The chromogenic precipitate is optically enhanced by brief immersion of stained sections in 0.125% (w/v) osmium tetroxide. The section is then rinsed in tap water, counterstained in Harris' hematoxylin, dehydrated in graded ethanols and Americlear, and mounted in a synthetic mounting medium.

After the second biotinylated antibody is incubated and washed, slides for acoustic microscopy are incubated in avidin (1.0 mg/~20 cc PBS) using a bath on a rotating table for 30 min. Excess avidin is washed away with isotonic PBS buffer, pH 7.4–7.5 in three minute washes. Slides are incubated with biotinylated or control perfluorocarbon emulsion for twenty minutes (0.5 cc/~20.0 ml PBS), washed briefly with isotonic PBS 3× for 5 minutes each and reincubated with avidin (1.0 mg/~20 cc) for 15 minutes. Excess avidin is rinsed off with three, 5 min. washes in PBS. The slide is then reincubated at above concentrations with biotinylated or control perfluorocarbon emulsion for 20 minutes. Unbound emulsion is washed away in three changes of PBS (5 minutes each) and the slides are transferred to the acoustic microscope for analysis.

The mounted specimens are each immersed into isotonic, phosphate buffered saline at room temperature for ultrasonic insonification. A custom designed acoustic microscope is used to collect ultrasonic data. The microscope consists of 50 MHz broadband, focused, piezoelectric delay-line transducer (¼ inch diameter, ½ inch focal length, 62 micron beam diameter, Model V390, Panametrics Co., Waltham, Mass.) operated in the pulse-echo mode. A Tektronix DSA 601 digitizing oscilloscope (Beaverton, Oreg.) is used to digitize 35 degree polar backscattered radio frequency (rf) data at 500 megasamples per second with 8-bit resolution. A variable gain system is used to increase the effective dynamic range of this digitizer. Radio frequency data is acquired from approximately 100 independent sites from each specimen with 50 micron lateral step resolution.

The rf data is stored in a low resolution raster scan format and analyzed with custom software. Segments of the rf lines are gated for integrated backscatter analysis to encompass the front surface (i.e. excluding the back wall). The gated data are multiplied by a Hamming window and their power spectra are determined by fast-Fourier transformation. Power spectra within a tissue section are compared directly without reference to a steel plate. Integrated backscatter (IB) is computed from the average of the frequency-dependent backscatter transfer function across the useful bandwidth of the transducer (30 to 55 MHz). Immunostained tissues are reviewed using a Nikon Optiphot-2 microscope for regions of PSA positive staining and the acoustic characteristics are compared.

The net change in the apparent backscatter transfer function between the normal prostatic stroma and carcinomatous regions are clearly increased in sections treated with PSA targeted biotinylated versus the control perfluorocarbon emulsion across the frequency spectrum (30 to 55 MHz; FIG. 12). Biotinylated perfluorocarbon emulsion increases ($p<0.05$) the integrated backscatter from regions of prostatic cancer (47.17±dB) versus normal stromal (40.79±1.18 dB) by 6.38 dB (approximately 4-fold). In the control tissue sections, the integrated backscatter from the region of prostatic carcinoma (39.63±1.63 dB) was greater ($p<0.05$) than that from the normal stromal areas (36.13±2.17 dB) by approximately 3.5 dB (2-fold), reflecting inherent differences in acoustic character between normal and cancerous prostatic tissue. However, the targeted biotinylated perfluorocarbon emulsion amplified ($p<0.05$) these inherent differences by approximately 2-fold (2.87 dB; FIG. 13). These results clearly demonstrate the ability of site-targeted biotinylated perfluorocarbon emulsion to specifically enhance acoustic detection of prostate cancer in vitro.

EXAMPLE 11

Biotinylated perfluorocarbon emulsion, approximately 250 nm diameter, is targeted to ovarian carcinoma using monoclonal antibodies specific for OC-125 antigen and are acoustically detected using polar, high frequency, high resolution acoustic microscopy. Representative examples of human ovarian, carcinoma tissues are routinely processed by immersion fixation in 10% neutral buffered formalin and embedded in paraffin. Twenty micron sections are prepared for acoustic microscopy; 5 micron sections are used for optical studies. All histologic sections are mounted on acid cleaned glass slides that have been coated with poly-L-lysine. All mounted sections are heated to 55° C. for 1 hour in an oven.

Prior to immunostaining, all sections are dewaxed in three changes of Americlear, and dehydrated in successive changes of 95% and 100% ethanol. Endogenous peroxidase activity is blocked only in sections prepared for optical studies by immersion in absolute methanol containing 0.6% (v/v) hydrogen peroxide for 30 minutes. These and all sections for acoustic microscopy are then rehydrated through graded ethanols and distilled water and placed in isotonic PBS (pH 7.4). All sections are incubated with target specific monoclonal antibodies.

Ovarian sections are incubated with anti-OC-125 primary monoclonal antibodies per the recommendations of the vendor for 18 hours at 4° C. in moisture chambers. After primary incubation, sections are rinsed in isotonic PBS, then overlain with a polyclonal biotinyl-horse anti-mouse immunoglobin (VectaStain Elite Kits, Vector Laboratories, Burlingame, Calif.) for 1 hour at room temperature. After rinsing in PBS, duplicate 30 micron sections are prepared for acoustic microscopy. Sections for light microscopy (5 micron) are incubated with avidin-biotin-peroxidase complex (VectaStain Elite Kit, Vector Lab) for 1 hour at room temperature. Sections are rinsed in phosphate buffer (pH 7.6) and immersed in a solution at 3,3'-diaminobenzidine tetrahydrochloride (Sigma Chemicals, St. Louis, Mo.; 0.5 mg/ml in phosphate buffer, pH 7.6, containing 0.0003% [v/v] hydrogen peroxide) for approximately ten minutes. The chromogenic precipitate is optically enhanced by brief immersion of stained sections in 0.125% (w/v) osmium tetroxide. Sections are then rinsed in tap water, counterstained in Harris' hematoxylin, dehydrated in graded ethanols and Americlear, and mounted in a synthetic mounting medium.

After the second biotinylated antibody is incubated and washed, slides are incubated in avidin (1.0 mg/~20 cc PBS) using a bath on a rotating table for 30 min. Excess avidin is washed away with isotonic PBS buffer, pH 7.4–7.5 in three 5 minute washes. The prepared slides are incubated with biotinylated or control perfluorocarbon emulsion for twenty minutes (0.5 cc/~20.0 ml PBS), washed briefly with isotonic PBS 3× for 5 minutes each and rewashed in avidin (1.0 mg/~20 cc) for 15 minutes. Excess avidin is rinsed off with three, 5 min. washes in PBS. Slides are then reincubated at above concentrations with biotinylated or control perfluorocarbon emulsion for 20 minutes. Unbound emulsion is washed away in three changes of PBS (5 minutes each) and the slides are transferred to the acoustic microscope for analysis.

The mounted specimens are each immersed into isotonic, phosphate buffered saline at room temperature for ultrasonic insonification. A custom designed acoustic microscope is used to collect ultrasonic data. The microscope consists of 50 MHz broadband, focused, piezoelectric delay-line transducer (¼ inch diameter, ½ inch focal length, 62 micron beam diameter, Model V390, Panametrics Co., Waltham, Mass.) operated in the pulse-echo mode. A Tektronix DSA 601 digitizing oscilloscope (Beaverton, Oreg.) is used to digitize 35 degree polar backscattered radio frequency (rf) data at 500 megasamples per second with 8-bit resolution. A variable gain system is used to increase the effective dynamic range of this digitizer. Radio frequency data is acquired from approximately 100 independent sites from each specimen with 50 micron lateral step resolution.

The rf data are stored in a low resolution raster scan format and analyzed with custom software. Segments of the rf lines are gated for integrated backscatter analysis to encompass the front surface (i.e. excluding the back wall). The gated data are multiplied by a Hamming window and their power spectra are determined by fast-Fourier transformation. Integrated backscatter is computed from the average of the frequency-dependent backscatter transfer function across the useful bandwidth of the transducer (30 to 55 MHz). The power spectra from the specimens are referenced to the power spectrum returned from a glass microscope slide. IB is expressed in decibels relative to the scattering from the glass slide. Immunostained tissues are reviewed using a Nikon Optiphot-2 microscope for regions of PSA positive staining and the acoustic characteristics are compared.

The net change in the apparent backscatter transfer function between the normal ovarian stroma and carcinomatous regions are clearly increased in sections treated with OC-125 targeted biotinylated versus the control perfluorocarbon emulsion across the frequency spectrum (30 to 55 MHz; FIG. 14). Biotinylated perfluorocarbon emulsion increases ($p<0.05$) the integrated backscatter from regions of ovarian cancer ($-28.19\pm1.39$ dB) versus normal stromal ($-38.75\pm0.84$ dB) by 10.57 dB (greater than 8-fold). In the control tissue sections, the integrated backscatter from the region of ovarian carcinoma ($-33.49\pm0.86$ dB) was greater ($p<0.05$) than the normal stromal areas ($-40.21\pm0.61$ dB), approximately 6.72 dB (4-fold), reflecting inherent inherences in acoustic character between normal and cancerous ovarian tissue. However, the targeted biotinylated perfluorocarbon emulsion amplified ($p<0.05$) these inherent differences by approximately 2-fold (3.84 dB; FIG. 15). These results clearly demonstrate the ability of site-targeted biotinylated perfluorocarbon emulsion to specifically enhance acoustic detection of ovarian cancer in vitro.

EXAMPLE 12

Biotinylated perfluorocarbon emulsion, approximately 250 nm diameter, is targeted to the epithelial capsule of tonsil using monoclonal antibodies specific for cytokeratin, CD-20, and BCL-2 antigens and are acoustically detected using polar, high frequency, high resolution acoustic microscopy. Representative examples of human tonsil are routinely processed by immersion fixation in 10% neutral buffered formalin and embedded in paraffin. Twenty micron sections are prepared for acoustic microscopy; a 5 micron section is used for optical studies. All histologic sections are mounted on acid cleaned glass slides that have been coated with poly-L-lysine. All mounted sections are heated at 55° C. for 1 hour in an oven.

Prior to immunostaining, all sections are dewaxed in three changes of Americlear, and dehydrated in successive changes of 95% and 100% ethanol. Endogenous peroxidase activity is blocked only in sections prepared for optical studies by immersion in absolute methanol containing 0.6% (v/v) hydrogen peroxide for 30 minutes. These and all sections for acoustic microscopy are then rehydrated through graded ethanols and distilled water and placed in isotonic PBS (pH 7.4). All sections are incubated with target specific monoclonal antibodies.

Tonsil sections are incubated with a mixture of anti-CD-20, BCL-2, and cytokeratin primary monoclonal antibodies per the recommendations of the vendor for 18 hours at 4° C. in moisture chambers. After primary incubation, sections are rinsed in isotonic PBS, then overlain with a polyclonal biotinyl-horse anti-mouse immunoglobin (VectaStain Elite Kits, Vector Laboratories, Burlingame, Calif.) for 1 hour at room temperature. After rinsing in PBS, duplicate 30 micron sections are prepared for acoustic microscopy. Sections for light microscopy (5 micron) are incubated with avidin-biotin-peroxidase complex (VectaStain Elite Kit, Vector Lab) for 1 hour at room temperature. Sections are rinsed in phosphate buffer (pH 7.6) and immersed in a solution of 3,3'-diaminobenzidine tetrahydrochloride (Sigma Chemicals, St. Louis, Mo.; 0.5 mg/ml in phosphate buffer, pH 7.6, containing 0.003% [v/v] hydrogen peroxide) for approximately ten minutes. The chromogenic precipitate are optically enhanced by brief immersion of stained sections in 0.125% (w/v) osmium tetroxide. Sections are then rinsed in tap water, counterstained in Harris, hematoxylin, dehydrated in graded ethanols and Americlear, and mounted in a synthetic mounting medium.

After the second biotinylated antibody is incubated and washed, one slide is incubated in avidin (1.0 mg/~20 cc PBS) using a bath on a rotating table for 30 min. Excess avidin is washed away with isotonic PBS buffer, pH 7.4–7.5 in three 5 minute washes. The prepared slide is incubated with biotinylated perfluorocarbon emulsion for twenty minutes (0.5 cc/~20.0 ml PBS), washed briefly with isotonic PBS 3× for 5 minutes each and rewashed in avidin (1.0 mg/~20 cc) for 15 minutes. Excess avidin is rinsed off with three, 5 minute washes in PBS. The slides are reincubated at above concentrations with biotinylated perfluorocarbon emulsion for 20 minutes. Unbound emulsion is washed away in three changes of PBS (5 minutes each) and the slide is transferred to the acoustic microscope for analysis.

The mounted specimen is immersed into isotonic, phosphate buffered saline at room temperature for ultrasonic insonification. A custom designed acoustic microscope is used to collect ultrasonic data. The microscope consists of a 50 MHz broadband, focused, piezoelectric delay-line transducer (¼ inch diameter, ½ inch focal length, 62 micron beam diameter, Model V390, Panametrics Co., Waltham, Mass.) operated in the pulse-echo mode. A Tektronix DSA 601 digitizing oscilloscope (Beaverton, Oreg.) is used to digitize 35 degree polar backscattered radio frequency (rf) data at 500 megasamples per second with 8 bit resolution. A variable gain system is used to increase the effective dynamic range of this digitizer. Radio frequency data are collected from the entire specimen and a peak detected image is created of the section and compared with the immunostained tissue image.

Immunostained tissue is examined and imaged using a Nikon Optiphot-2 microscope with a Javlin Chromachip II camera attachment. Images are routed through a Panasonic digital mixer model WJ-AVE5 to Panasonic SVHS video recorders, models AG-1960 or AG-1970 and displayed upon an Sony Trinitron monitor. Images are captured using NuVista software (Truevision, Inc., Indianapolis, Ind. 46256) executing on a Macintosh LCIII microcomputer.

FIG. 16 compares tonsil acoustically imaged as a radio frequency peak detected scan at 100 micron lateral step resolution (a) with an optically imaged section immunostained with horseradish peroxidase (b). The epithelial capsule targeted by a mixture of anti-cytokeratin antibodies is distinctly stained with horseradish peroxidase and homologous regions in the acoustic image are "brightened" by the targeted biotinylated acoustic contrast. In FIG. 17 the radio frequency peak detected acoustic image at 100 micron step resolution (a) is enhanced to 50 micron lateral step resolution. The targeted biotinylated perfluorocarbon contrast is clearly seen acoustically enhancing the epithelial rim of the tonsil, analogous to the optical immunostained image. This example clearly demonstrates the fidelity of biotinylated perfluorocarbon contrast targeting for enhanced acoustic contrast of tissues, such as lymph nodes.

EXAMPLE 13

Method to Prepare Control and Biotinylated Perfluorocarbon Microemulsions Incorporating Gadolinium DTPA into the Outer Lipid Membrane The biotinylated perfluorocarbon contrast agent was produced by incorporating biotinylated phosphatidylethanolamine into the outer lipid monolayer of a perfluorocarbon microemulsion. Briefly, the emulsion was comprised of perfluorodichlorooctane (40%, v/v, PFDCO, Minnesota Manufacturing and Mining, St. Paul, Minn.), safflower oil (2.0%, w/v), a surfactant co-mixture (2.0%, w/v) and glycerin (1.7%, w/v). The surfactant co-mixture include (50 to 70 mole % lecithin (Pharmacia Inc., Clayton, N.C.), 0 to 35 mole % cholesterol (Sigma Chemical Co. St. Louis, Mo.) and 0.5 to 1 mole % N-(6-(biotinoyl)amino)hexanoyl)-dipalmitoyl-L-alpha-phosphatidylethanolamine Pierce, Rockford, Ill.) and 0 to 30% gadolinium (diethylenetriaminepentaacetic acid bis(oleylamide) (Gd-DTPA-BOA), (Gateway Chemical Technology, St. Louis, Mo.) which were dissolved in chloroform. The chloroform-lipid mixture was evaporated under reduced pressure, dried in a 50° C. vacuum oven overnight and dispersed into water by sonication, resulting in a liposome suspension. The liposome suspension was transferred into a blender cup (dynamics Corporation of America, New Hartford, Conn.) with perfluorodichlorooctane, safflower oil and distilled, deionized water and emulsified for 30 to 60 seconds. The emulsified mixture was transferred to an S100 Microfluidics emulsifier (Microfluidics, Newton, Mass.) and continuously processed at 10,000 PSI for three minutes. The completed emulsion was vialed, blanketed with nitrogen and sealed with stopper crimp seal until use. A control emulsion was prepared identically except a nonbiotinylated phosphatidylethanolamine was substituted into the surfactant co-mixture. Biotinylated and control perfluorocarbon emulsion particle sizes were determined in triplicate at 37° C. with a Brookhaven BI-90 laser light scatter submicron particle size analyzer (Brookhaven Instruments Corporation, Holtsville, N.Y.).

EXAMPLE 14

Demonstration of the Effect of Gadolinium Incorporation on Increases in Particle Size Associated with Avidin Addition Biotinylated, gadolinium DTPA perfluorocarbon emulsions (30 µl) were added to 2.97 ml of isotonic phosphate buffered saline (PBS), pH 7.4 and avidin in a polystyrene cuvette. Avidin (Pierce, Inc., Rockford, Ill.) was dissolved in PBS and was present in the cuvette to final concentrations of 0 to 10 µg/ml. All samples were prepared in duplicate, were mixed by gentle inversion, and continuously agitated at low speed on a rotary table for 30 minutes at room temperature. Emulsion particles sizes were determined in triplicate at 37° C. with a Brookhaven BI-90 laser light scatter submicron particle size analyzer (Brookhaven Instruments Corporation, Holtsville, N.Y.). FIG. 18 reveals that the baseline particle size for three emulsions incorporating gadolinium remained around 250 nm. Addition of avidin increased particle size in a dose related manner. Incremental increases in emulsion particle size were slightly but not detrimentally smaller for the higher concentrations of gadolinium incorporation.

EXAMPLE 15

Figure 19:
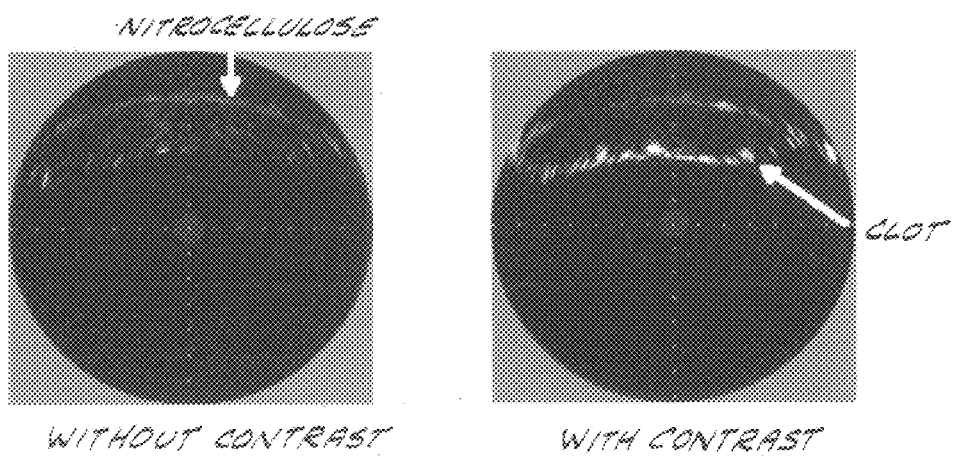
FIG. 19 shows the enhancement of the acoustic reflectivity of plasma clots treated with targeted perfluorocarbon dual ultrasonic and MRI contrast.

Demonstrates the Ability of Biotinylated Perfluorocarbon Emulsions Incorporating Gadolinium DTPA into their Outer Membrane to Target and Acoustically Enhance Human Plasma Clots Whole human blood was obtained fresh and anticoagulated (9:1, v/v) with sterile sodium citrate. In a series of trials, plasma clots (6) were produced by combining plasma and 100 mM calcium chloride (3:1 v/v) with 5 units of thrombin (Sigma Chemical Company, St. Louis, Mo.) in a plastic mold on a nitrocellulose surface. The plasma was allowed to coagulate slowly at room temperature. Half of the clots (3) were incubated individually with 150 µg biotinylated antifibrin monoclonal antibody (NIB 5F3; NIBSC, Herts, United Kingdom) in 10 ml PBS for two hours; the remaining clots (3) were maintained in PBS. The antibody treated clots were then incubated with avidin (50 µg/ml PBS) for 30 minutes followed by 10% gadolinium, biotinylated perfluorocarbon emulsion (30 µl/ml PBS for 30 minutes. The control clots were treated similarly with control perfluorocarbon emulsion (30 µl/ml PBS). Targeted and control clots were retreated with avidin and targeted or control perfluorocarbon emulsion, respectively, to optimize surface saturation prior to ultrasonic interrogation. Clots on nitrocellulose disks were placed in a waterbath and imaged with 30 MHz intravascular catheters (Boston Scientific Corporation, Maple Grove, Minn.) and a conventional ultrasonic scanner with a 7.5 MHz linear array transducer (Hewlett Packard Inc.) Ultrasonic images were recorded on to Super-VHS videotape for subsequent image analysis. FIG. 19 clearly demonstrates the enhanced acoustic reflectivity of the plasma clot surface with the target acoustic contrast which is not appreciated in the control. These results demonstrate that the targeting capability and the enhanced acoustic reflectivity effects of the biotinylated perfluorocarbon emulsion was retained.

EXAMPLE 16

The Efficacy of the Dual Ultrasound/MRI Contrast Agent in Solution to Provide T1 Shortening in a Concentration Dependent Manner Biotinylated emulsions incorporating gadolinium DTPA at overall concentrations of 0.2, 0.4 and 0.6 mole-% into the outer lipid membrane were prepared as described in Example 13. The dual contrast particles were serially diluted with PBS into 3 cc plastic tubes and magnetic resonance imaging was performed using a Philips Gyroscan S15 ACS-NT (1.5T). A Look-Locker MR pulse sequence was used to map the longitudinal relaxation curve. Briefly, an inversion pulse was applied, followed by acquisition of a series of images with small flip angles and short inter-image spacing. The signal intensity changes between images were directly related to the actual relaxation curve, and T1 (the spin-lattice relaxation time) was determined from this relationship. The pulse sequence parameters used in this experiment were TR 50 ms, TE 10 ms, flip angle 5 degrees, matrix 64×64, field of view 160×104 mm, 20 images, delay after inversion pulse 16 ms. The experiment was repeated with a Tr of 25 ms in order to measure very short T1's at high $GD^{3+}$ concentration. T1 parametric maps were generated where pixel intensity is the T1 value in milliseconds. Table 1 reveals the direct dependence of T1 shortening on gadolinium concentration. T1 shortening was greater for particles containing higher concentrations of gadolinium whether achieved by formulation or dilution.

TABLE 1

T1 dependence on Gd concentration

| Formulation Dilution | 0.2% Gd [Gd] mM | T1 (ms) | 0.4% Gd [Gd] mM | T1 (ms) | 0.6% Gd [Gd] mM | T1 (ms) |
|---|---|---|---|---|---|---|
| 1:16 (2.5% PFC) | 0.000125 | 972 ± 2 | 0.000252 | 492 ± 1 | 0.000314 | 519 ± 1 |
| 1:8 (5% PFC) | 0.000249 | 878 ± 7 | 0.000505 | 339 ± 2 | 0.000628 | 414 ± 4 |
| 1:4 (10% PFC) | 0.000498 | 430 ± 7 | 0.00101 | 189 ± 2 | 0.001256 | 156 ± 2 |
| 1:2 (20% PFC) | 0.000996 | 169 ± 1 | 0.00202 | 92 ± 1 | 0.002511 | 90 ± 1 |
| 1:1 (40% PFC) | 0.001992 | 65 ± 1 | 0.00404 | <50 | 0.005022 | <50 |

The control emulsion (i.e. no gadolinium) had a mean %1 of 1788±9 ms. T1's shorter 50 ms than could not be resolved with the present technique. The relaxivity for each preparation (0.2%, 0.4%, and 0.6% [Gd]) was determined by computing the slope of the line relating [Gd] in mM to 1/%1 (Table 2). The relativity of the 0.2 gadolinium emulsions was the greatest; whereas, the relaxivity of the 0.4% and 0.6 contrast formulations were shorter and similar.

TABLE 2

Relaxivity of preparations

| | slope (ms-mM) | intercept | r |
|---|---|---|---|
| 0.2% | 7.89 | −0.00093 | 0.99 |
| 0.4% | 5.06 | 0.00049 | 0.99 |
| 0.6% | 4.36 | 0.00034 | 0.99 |

EXAMPLE 17

The Efficacy of the Dual Ultrasound/MRI Contrast Agent Targeted In Vitro to Human Plasma Clots to Provide T1 Shortening Biotinylated emulsions incorporating gadolinium at overall concentrations of 10, 20 and 30 mole % into the outer lipid membrane were prepared as described in Example 13. The actual weight percentage of gadolinium in the applied emulsions are 0.25% (10%), 0.43% (20%), and 0.54% (30%). Whole human blood was obtained fresh and anticoagulated (9:1, v/v) with sterile sodium citrate. In a series of trials, plasma clots (6) were produced by combining plasma and 1000 mM calcium chloride (3:1, v/v) with 5 units of thrombin (Sigma Chemical Company, St. Louis, Mo.) in a plastic mold on a nitrocellulose surface. The clot dimensions when formed on the nitrocellulose support membrane were: thickness<0.5 mm; diameter ~1 cm. The plasma was allowed to coagulate slowly at room temperature. Half of the clots (3) were incubated individually with 150 μg biotinylated antifibrin monoclonal antibody (NIB 5F3; NIBSC, Herts, United Kingdom) in 10 ml PBS for two hours; the remaining clots (3) were maintained in PBS. The antibody treated clots were then incubated with avidin (50 μg/ml PBS) for 30 minutes followed by 10% gadolinium, biotinylated perfluorocarbon emulsion (30 μl/ml PBS) for 30 minutes. The control clots were treated similarly with control perfluorocarbon emulsion (30 μl/ml PBS). Half of the targeted and control clots were retreated with avidin and targeted or control perfluorocarbon emulsion, respectively, to optimize surface saturation prior to imaging.

Clots exposed to control and targeted gadolinium contrast were encased with 10% gelatin in P-30, plastic petri dishes and magnetic resonance imaging was performed using a Philips Gyroscan S15 ACS-NT (1.5T). A Look-Locker pulse sequence was used to map the longitudinal relaxation curve. Briefly, an inversion pulse was applied, followed by acquisition of a series of images with small flip angles and short inter-image spacing. The pulse sequence parameters were TR 50 ms, TE 10 ms, flip angle 5 degrees, matrix 64×64, field of view 160×104 mm, 20 images, delay after inversion pulse 16 ms. T1 was determined from the resulting parametric T1 map in each clot and in the surrounding gel. T2 (spin-spin relaxation time) was determined from an 8 echo spin-echo sequence with TE 30 ms, and TR 8000 ms. The image voxel dimension for this experiment was ~2.5×2.0× 2.0 mm.

The mean T1 value for the gel was 582±8 ms. T2 values for all samples fell in a narrow range between 80 and 92 ms. T2 of the gel was 91 ms. Adding Gd to the preparation resulted in a measurable and significant drop in T1 which plateaued at the lowest paramagnetic concentration (Table 3). Because of the partial volume effect involved in this measurement (i.e., only a thin layer of gadolinium emulsion on a clot surface relative to the voxel dimension, or approximately 11:1 gel substrate to gadolinium-emulsion), the contrast enhancement effect is actually remarkably sensitive.

TABLE 3

T1 dependence on [Gd] targeted to fibrin clots imbedded in gelatin.

| [Gd] | 1 exposure to targeting system | 2 exposures to targeting system |
|---|---|---|
| 0.0% | 725 ± 16 | 824 ± 41 |
| 0.25% | 662 ± 23 | 696 ± 15 |
| 0.43% | 642 ± 21 | 660 ± 11 |
| 0.54% | 666 ± 17 | 667 ± 13 |

EXAMPLE 18

In Situ Targeting of Canine Thrombi In Vivo for Magnetic Resonance Imaging Using Dual Contrast Agent In accordance with approved animal protocols, dogs weighing 20–30 Kg were anesthetized with sodium pentobarbital (30 mg/kg, i.iv.) followed by 1% halothane in oxygen. The right femoral artery and all branches between the inguinal ligament and the saphenous artery were exposed. One proximal arterial branch, slightly distal to the inguinal ligament, was selected for cannulation. All other branches were ligated. The tip of a 23 ga needle crimped on silver plated copper wire was inserted obliquely into the femoral artery 2–3 cm proximal to the saphenous branch and secured with 4–0 Prolene suture through connective tissue on either side. Anodal current (200–400 μA) was applied for 90 to 120 minutes to induce a partially occlusive thrombus. A Doppler flow probed placed proximally was used to monitor the development of thrombus. Partial distal constriction of the femoral artery was used to facilitate thrombus formation.

After a thrombus had been formed, a 20 ga. catheter was inserted into the preserved proximal branch of the artery and a pressurized 0.9% NaCl drip was attached through a three-way stopcock to the catheter. Saline was allowed to flush the artery and antegrade blood flow through the femoral artery was stopped by placement of a snare 1–2 cm proximal to the catheter. Continued blood flow through the distal femoral arterial containing the thrombus was prevented for the duration of the study. After blood was flushed from the isolated arterial segment with continuous saline infusion, the distal femoral artery was occluded transiently with a snare. For contrast targeted thrombi, biotinylated antifibrin monoclonal antibody (150 µg NIB 5F3 or NIB 1H10 in 0.5 ml of PBS, pH 7.2–7.4) was injected through the three-way stopcock and incubated in the vessel for one hour. The distal snare on the femoral artery was then released and unbound antibody was flushed away with 0.9% saline. After re-establishing the distal arterial occlusion, 0.5 mg of avidin (Pierce, Rockford, Ill.) in 0.5 ml of PBS was injected into the segment and incubated within artery for 30 minutes. Again, the distal occlusion was released and unbound avidin was flushed from the lumen with 0.9% NaCl. The distal arterial occlusion was re-established and 0.2 ml of biotinylated emulsion was injected into the vessel lumen and incubated for 30 minutes.

Arteries were ultrasonically imaged after thrombus formation (baseline and after each administration of antibody, avidin and perfluorocarbon emulsion with a 7.5 M.Hz linear array transducer using a commercially available imaging system. The acoustically reflective needle electrode was used to localize regions of thrombosis for insonification. After all data were collected, the presence of thrombus was confirmed in each animal by incision of the artery at the end of study.

After ultrasonic imaging, the femoral arterial segment was perfused with formalin in situ for 30 minutes and then excised with a rigid support to preserve conformation. The arterial segment was placed in a formalin container and transferred to the MRI scanner for imaging. Magnetic resonance imaging was performed using a Philips Gyroscan S15 ACS-NOT (1.5T) using the Look-Locker technique with a TR of 100 ms, TE 10 ms, flip angle 5 degrees, matrix 64×64, field of view 160×104 mm, 20 images, delay after inversion pulse 16 ms. Slice thickness was 4 mm.

Figure 20:
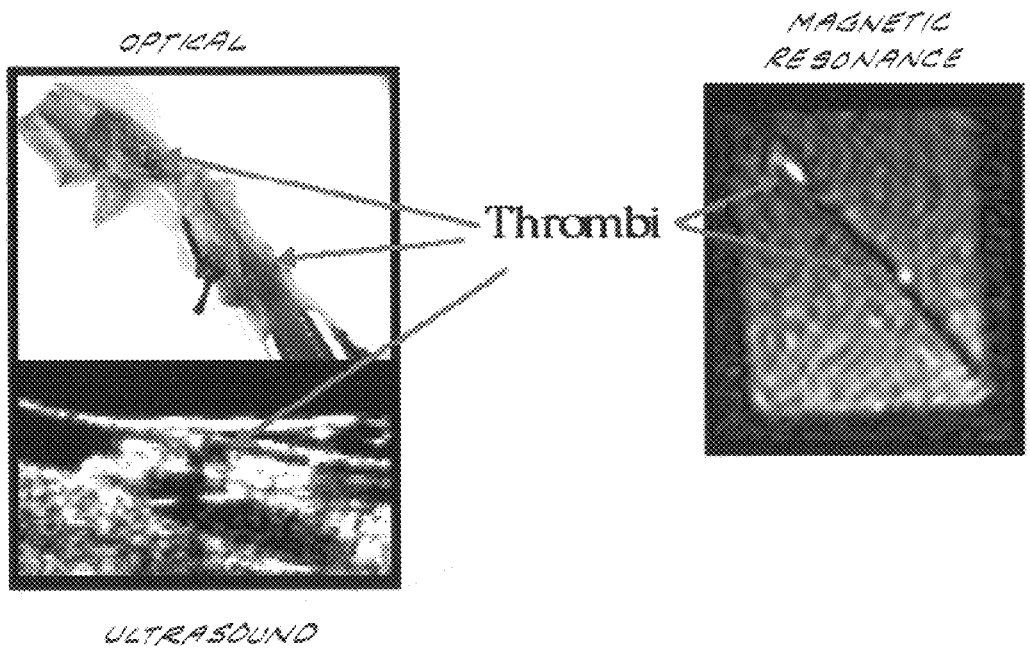
FIG. 20 shows the femoral artery thrombus detected by both magnetic resonance and ultrasound.

The measured T1 of the formalin background was 2319±12 ms, and the measured T1 of the thrombus was 1717±173 ms. This difference in T1 between the clot and background resulted in high contrast as shown in FIG. 20. The location and dimensions of the enhanced T1 signal were analogous to the result obtained by ultrasound FIG. 20 and confirmed dissection of the artery. A second arterial thrombus preparation imaged with the same magnetic resonance techniques yielded analogous results. In this experiment, the T1 of the clot was 1572±173 ms, and the background T1 was 2319±12 ms.

In view of the above, it will be seen that the several objects of the invention are achieved and other advantageous results attained.

EXAMPLE 19

Stannous (II) Chloride Method to Prepare Control and Biotinylated Perfluorocarbon Microemulsions Incorporating $^{99m}$Tc into the Lipid Membrane The biotinylated perfluorocarbon contrast agent was produced by incorporating biotinylated phosphatidylethanolamine into the outer lipid monolayer of a perfluorocarbon microemulsion as previously demonstrated. Briefly, the emulsion is comprised of perfluorodichlorooctane (40% v/v, PFDCO, Minnesota Manufacturing and Mining, St. Paul, Minn.), safflower oil (2.0%, w/v), a surfactant co-mixture (2.0%, w/v) and glycerin (1.7% w/v). The surfactant co-mixture included 50–70 mole % lecithin (Pharmacia Inc., Clayton, N.C.), 0 to 35 mole % cholesterol (Sigma Chemical Co., St. Louis, Mo.) and 0.5 to 1 mole % N-(6-biotinoyl) amino)hexanoyl)-dipalmitoyl-L-alpha-phosphatidylethanolamine Pierce, Rockford, Ill.) which is dissolved in chloroform. The chloroform-lipid mixture is evaporated under reduced pressure, dried in a 50° C. vacuum oven overnight and dispersed into water by sonication, resulting in a liposome suspension. The liposome suspension is transferred into a blender cup (Dynamics Corporation of America, New Hartford, Conn.) with perfluorodichlorooctane, safflower oil, glycerin, and distilled, deionized water and emulsified for 30 to 60 seconds. The emulsified mixture is transferred to an S110 Microfluidics emulsifier (Microfluidics, Newton, Mass.) and continuously processed at 10,000 PSI for three minutes. The completed emulsion is vialed, blanketed with nitrogen and sealed with stopper crimp seal until use. A control emulsion is prepared identically except a nonbiotinylated phosphatidylethanolamine is substituted into the surfactant co-mixture. Biotinylated and control perfluorocarbon emulsion particle sizes are determined in triplicate at 37° C. with a laser light scatter submicron particle size analyzer.

Stannous (II) chloride (SnCl$_2$•2H$_2$O) 2 to 10 mmol/l in NaCl 150 mmol/l and 1 to 10 mCi of $^{99m}$Tc-pertechnetate may be combined with 1 to 3 g of a 40% perfluorocarbon emulsion with 2% lipid surfactant (as described above) for 30 minutes at room temperature. Unbound $^{99m}$Tc-pertechnetate may be removed by repeated centrifugation and washing of the emulsion with NaCl 150 mmol/l or by routine column chromatography (Sepharose 4B or equivalent). Labelling efficiencies (%) are obtained by the ratio of counts per minute in the emulsion pellet/total counts per minute added×100 or by counts per minute eluting with the particles from the column/total counts per minute engaged on the chromatography column.

EXAMPLE 20

Stannous Oxinate Method to Prepare Control and Biotinylated Perfluorocarbon Microemulsions Incorporating $^{99m}$Tc into the Lipid Membrane The biotinylated perfluorocarbon contrast agent was produced by incorporating biotinylated phosphatidylethanolamine into the outer lipid monolayer of a perfluorocarbon microemulsion as demonstrated previously. Stannous oxinate is added to the lipid surfactant for direct incorporation into the lipid membrane. Brief, the emulsion was comprised of perfluorodichlorooctane (40% v/v, PFDCO, Minnesota Mining and Manufacturing, St. Paul, Minn.), safflower oil (2.0%, w/v, optional), a surfactant co-mixture (2.0%, w/v) and glycerin (1.7%, w/v). The surfactant co-mixture included (50 to 70 mole % lecithin (Pharmacia Inc., Clayton, N.C.), 0 to 35 mole % cholesterol (Sigma Chemical Co., St. Louis, Mo.) and 0.5 to 1 mole % N-(6-(biotinoyl)amino) hexanoyl)-dipalmitoyl-L-alpha-phosphatidylethanolamine Pierce, Rockford, Ill.), and stannous oxinate (500 µg) which were dissolved in chloroform or chloroform/methanol. The chloroform-lipid mixture was evaporated under reduced pressure, dried in a 50° C. vacuum oven overnight and dispersed into water by sonication, resulting in a liposome suspension. The liposome suspension was transferred into a blender cup (Dynamics Corporation of America, New Hartford, Conn.) with perfluorodichlorooctane, safflower oil (optional), glycerin, and distilled, deionized water and emulsified for 30 to 60 seconds. The emulsified mixture was transferred to an S110 Microfluidics emulsifier (Microfluidics, Newton, Mass.) and continuously processed at 10,000 PSI for three minutes. The completed emulsion was vialed, blanketed with nitrogen and sealed with stopper crimpseal until use. A control emulsion was prepared identically except a nonbiotinylated phosphatidylethanolamine was substituted into the surfactant co-mixture. Biotinylated and control perfluorocarbon emulsion particle sizes were determined in triplicate at 37° C. with a laser light scatter submicron particle size analyzer.

Emulsion particles (2.5 g of 40% emulsion—approximately 20 mg lipid surfactant), washed by centrifugation of free stannous oxinate, is combined with $^{99m}$Tc technetate (3 to 10 mCi) for 30 minutes in room temperature. Unbound $^{99m}$Tc-pertechnetate is removed by repeated centrifugation and washing of the emulsion with NaCl 150 mmol/l or by routine column chromatography (Sepharose 4B or equivalent). Labelling efficiencies (%) are obtained by the ratio of counts per minute in the emulsion pellet/total counts per minute added ×100 or by counts per minute eluting with the particles from the column/total counts per minute engaged on the chromatography column.

EXAMPLE 21

Method to Prepare Control and Biotinylated Perfluorocarbon Microemulsions Incorporating $^{99m}$Tc into the Lipid Membrane Using Exametazine The biotinylated perfluorocarbon contrast agent was produced by incorporating biotinylated phosphatidylethanolamine into the outer lipid monolayer of a perfluorocarbon microemulsion. Briefly, the emulsion was comprised of perfluorodichlorooctane (40% v/v, PFDCO, Minnesota Mining and Manufacturing, St. Paul, Minn.), safflower oil (2.0%, w/v), a surfactant co-mixture (2.0% w/v) and glycerin (1.7%, w/v). The surfactant co-mixture included 50 to 70 mole % lecithin (Pharmacia In., Clayton, N.C.), 0 to 35 mole % cholesterol (Sigma Chemical Co., St. Louis, Mo.) and 0.5 to 1 mole % N-(6-biotinyoyl)amino)hexanoyl)-dipalmitoyl-L-alpha-phosphatidylethanolamine Pierce, Rockford, Ill.) which were dissolved in chloroform. The chloroform-lipid mixture was evaporated under reduced pressure, dried in a 50° C. vacuum oven overnight and dispersed into water by sonication, resulting in a liposome suspension. The liposome suspension was transferred into a blender cup (Dynamics Corporation of America, New Hartford, Conn.) with perfluorodichlorooctane, safflower oil, glycerin, and distilled, deionized water and emulsified for 30 to 60 seconds. The emulsified mixture was transferred to an S110 Microfluidics emulsifier (Microfluidics, Newton, Mass.) and continuously processed at 10,000 PSI for three minutes. The completed emulsion was vialed, blanketed with nitrogen and sealed with stopper crimp seal until use. A control emulsion was prepared identically except a non-biotinylated phosphatidylethanolamine was substituted into the surfactant co-mixture. Biotinylated and control perfluorocarbon emulsion particle sizes were determined in triplicate at 37° C. with a laser light scatter submicron particle size analyzer.

An HM-PAO (exametazine) kit (Ceretec®, Nycomed Amersham Inc., Arlington Heights, Ill.) containing 0.5 mg HMPAO and 4.0 μg SnCl$_2$ is reconstituted with 5–10 mCi of $^{99m}$TcO$_4$ in 5 ml of 0.9% NaCl and incubated for 5 minutes. One ml aliquot of $^{99m}$Tc-HMPAO were incubated with 5 ml of perfluorocarbon emulsion for 15 minutes. The mixture was centrifuged and washed with phosphate buffered saline. Labelling efficiencies (%) are obtained by the ratio of counts per minute in the emulsion pellet/total counts per minute added ×100.

EXAMPLE 22

Demonstration of the Effect of $^{99m}$Tc-pertechnetate Incorporation on Increases in Particle Size Associated with Avidin Addition Biotinylated, $^{99m}$Tc-perfluorocarbon emulsions (30 μl) are added to 2.97 ml of isotonic phosphate buffered saline (PBS), pH 7.4 and avidin in a polystyrene cuvette. Avidin (Pierce, In., Rockford, Ill.) was dissolved in PBS and was present in the cuvette to final concentrations of 0 to 10 μg/ml. All samples were prepared in duplicate, were mixed by gentle inversion, and continuously agitated at low speed on a rotary table for 30 minutes at room temperature. Emulsion particle sizes were determined in triplicate at 37° C. with a laser light scatter submicron particle size analyzer. Addition of avidin increases particle size in a dose related manner as previously demonstrated for the ultrasonic and MRI emulsion preparations.

EXAMPLE 23

Demonstrates the Ability of Biotinylated Perfluorocarbon Emulsions Incorporating $^{99m}$Tc-pertechnetate into their Membrane to Target and Acoustically Enhance Human Plasma Clots Whole human blood is obtained fresh and anticoagulated (9:1, v/v) with sterile sodium citrate. In a series of trials, plasma clots (6) are produced by combining plasma and 100 mM calcium chloride (3:1 v/v) with 5 units of thrombin (Sigma Chemical Co., St. Louis, Mo.) in a plastic mold on a nitrocellulose surface. The plasma is allowed to coagulate slowly at room temperature. Half of the clots (3) are incubated individually with 150 μg biotinylated antifibrin monoclonal antibody (NIB 5F3; NIBSC, Herts, United Kingdom) in 10 ml PBS for two hours; the remaining clots (3) were maintained in PBS. All clots are incubated with avidin (50 μg/ml PBS) for 30 minutes followed by $^{99m}$Tc-pertechnetate, biotinylated perfluorocarbon emulsion (30 μg/ml PBS) for 30 minutes. Antibody targeted and control clots are retreated with avidin and targeted or control perfluorocarbon emulsion, respectively, to optimize surface saturation prior to ultrasonic interrogation and gamma counting. Clots on nitrocellulose disks are placed in a waterbath and imaged with 30 MHz intravascular catheters (Boston Scientific Corporation, Maple Grove, Minn.) and a conventional ultrasonic scanner (Hewlett Packard Inc.). Ultrasonic images are recorded onto Super-VHS videotape for subsequent image analysis. Enhanced acoustic reflectivity of the plasma clot surface noted with the targeted acoustic contrast is not appreciated in the control clots, as previously demonstrated.

The control and targeted clots are placed in a gamma counter and differences in radioactivity determined. Targeted clots bear significantly more radioactivity than control clots, demonstrating the specific targeting of $^{99m}$Tc with emulsion particle. The formulation provides for both acoustic and radioactive diagnostic imaging.

These results show that the addition of a radionuclide such as technetium-99m does not impair the binding of the emulsion particles to avidin or the ability of the particles to bind targeted pathologic tissue and does not interfere with the acoustic reflectivity enhancement imparted by the bound emulsion particles. Thus, these results are essentially analogous to the results previously demonstrated for gadolinium-DTPA-BOA except that $^{99m}$Tc has been substituted for the paramagnetic complex.

In view of the above, it will be seen that the several objects of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for nuclear imaging in vivo through ligand-based binding of an emulsion to a surface to be imaged comprising administering to said surface:
   a. a site-specific ligand conjugated with a biotin activating agent;
   b. an avidin activating agent; and
   c. an emulsion conjugated with a biotin activating agent, said emulsion having a radionuclide incorporated therein;
   whereby said ligand is conjugated to said emulsion through an avidin-biotin interaction and the resulting conjugate is bound to said surface for nuclear imaging thereof.

2. A method as set forth in claim 1 wherein said emulsion additionally contains a chemotherapeutic agent.

3. A method as set forth in claim 1 wherein said ligand is selected from the group consisting of antibodies, viruses, chemotherapeutic agents, receptor agonists and antagonists, antibody fragments, lectins, albumins, peptides, hormones, amino sugars, lipids, fatty acids, nucleic acids, and cells prepared or isolated from natural or synthetic sources.

4. A method as set forth in claim 3 wherein said antibody is a monoclonal antibody.

5. A method as set forth in claim 1 wherein said ligand is conjugated to said emulsion directly or indirectly through intervening chemical groups.

6. A method as set forth in claim 1 wherein said ligand is conjugated to an avidin activating agent selected from the group consisting of avidin, streptavidin and avidin analogs and conjugates.

7. A method as set forth in claim 1 wherein said emulsion has incorporated into its outer coating a biotinylated lipid compatible moiety.

8. A method as set forth in claim 7 wherein said biotinylated lipid compatible moiety is selected from the group consisting of a derivatized natural or synthetic phospholipid, a fatty acid, cholesterol, lysolipid, sphingomyelin, tocopherol, glucolipid, stearylamine, cardiolipin, a lipid with ether or ester linked fatty acids, and a polymerized lipid.

9. A method as set forth in claim 8 wherein said biotinylated lipid compatible moiety is conjugated to an avidin activating agent selected from the group consisting of avidin, streptavidin and avidin analogs.

10. A method as set forth in claim 1 wherein said emulsion contains a fluorocarbon.

11. A method as set forth in claim 10 wherein said fluorocarbon is perfluorodichlorooctane.

12. A method as set forth in claim 10 wherein said fluorocarbon is a fluorocarbon-hydrocarbon compound.

13. A method as set forth in claim 10 wherein said fluorocarbon is a perfluoroalkylated compound selected from the group consisting of ethers, polyethers and crown ethers.

14. A method as set forth in claim 1 wherein said radionuclide is technetium-99m.

15. A composition for use in nuclear imaging of a biological surface comprising a biotinylated lipid coated emulsion containing a radionuclide and a fluorochemical.

16. A composition as set forth in claim 15 wherein said fluorochemical is a fluorocarbon.

17. A composition as set forth in claim 16 wherein said fluorocarbon is selected from the group consisting of fluorocarbon-hydrocarbons, perfluoroalkylated ethers, polyethers and crown ethers.

18. A composition as set forth in claim 16 wherein said fluorocarbon is perfluorodichlorooctane.

19. A composition as set forth in claim 15 wherein said radionuclide is technetium-99m.

20. A composition formed in vivo and permitting nuclear imaging of a biological surface to which it is bound, said composition comprising:
   a. a site-specific ligand conjugated with a biotin activating agent;
   b. an avidin activating agent; and
   c. an emulsion conjugated with a biotin activating agent, said emulsion having a radionuclide incorporated therein, said ligand being conjugated to said emulsion through an avidin-biotin interaction with the resulting conjugate.

21. A composition as set forth in claim 20 wherein said emulsion contains a fluorochemical.

22. A composition as set forth in claim 21 wherein said fluorochemical is a fluorocarbon.

23. A composition as set forth in claim 20 wherein said ligand is selected from the group consisting of antibodies, viruses, chemotherapeutic agents, receptor agonists and antagonists, antibody fragments, lectins, albumins, peptides, hormones, amino sugars, lipids, fatty acids, nucleic acids, and cells prepared or isolated from natural or synthetic sources.

24. A composition as set forth in claim 23 wherein said ligand is a monoclonal antibody.

25. A composition as set forth in claim 20 wherein said radionuclide is technetium-99m.

* * * * *